US008044181B2

(12) United States Patent
Bebbington et al.

(10) Patent No.: US 8,044,181 B2
(45) Date of Patent: Oct. 25, 2011

(54) **ANTIBODIES TO THE PCRV ANTIGEN OF *PSEUDOMONAS AERUGINOSA***

(75) Inventors: Christopher R. Bebbington, San Mateo, CA (US); Kenneth Luehrsen, Half Moon Bay, CA (US); Geoffrey T. Yarranton, Burlingame, CA (US); Mark Baer, San Francisco, CA (US)

(73) Assignee: KaloBios Pharmaceuticals, Inc., South San Francisco, CA (US)

(*) Notice: Subject to any disclaimer, the term of this patent is extended or adjusted under 35 U.S.C. 154(b) by 55 days.

(21) Appl. No.: 12/325,806

(22) Filed: Dec. 1, 2008

(65) Prior Publication Data

US 2009/0191186 A1 Jul. 30, 2009

Related U.S. Application Data

(60) Provisional application No. 60/991,679, filed on Nov. 30, 2007.

(51) Int. Cl.

| | |
|---|---|
| ***C07K 17/00*** | (2006.01) |
| ***C07K 17/14*** | (2006.01) |
| ***C07K 16/00*** | (2006.01) |
| ***C12P 21/08*** | (2006.01) |

(52) U.S. Cl. ................ 530/387.1; 530/387.3; 530/391.1

(58) Field of Classification Search ........................ None
See application file for complete search history.

(56) References Cited

U.S. PATENT DOCUMENTS

| | | | |
|---|---|---|---|
| 5,219,996 | A | 6/1993 | Bodmer et al. |
| 5,864,019 | A | 1/1999 | King et al. |
| 6,815,540 | B1 | 11/2004 | Pluckthun et al. |
| 6,818,748 | B2 | 11/2004 | Fulton et al. |
| 6,827,935 | B2 | 12/2004 | Frank et al. |
| 7,141,393 | B2 | 11/2006 | Torigoe et al. |
| 7,294,753 | B2 | 11/2007 | Kloetzer et al. |
| 2005/0255552 | A1 | 11/2005 | Flynn et al. |
| 2006/0134098 | A1 | 6/2006 | Bebbington et al. |
| 2008/0108565 | A1 | 5/2008 | Winston, Jr. et al. |

FOREIGN PATENT DOCUMENTS

| | | | |
|---|---|---|---|
| WO | WO 02/064161 | A1 | 8/2002 |
| WO | WO 2006/122822 | A1 | 11/2006 |
| WO | WO 2006/125481 | A1 | 11/2006 |
| WO | WO 2007/003010 | A1 | 1/2007 |
| WO | WO 2007/096396 | A1 | 8/2007 |
| WO | WO 2007/148417 | A1 | 12/2007 |

OTHER PUBLICATIONS

Skolnick and Fetrow. From genes to protein structure and function: novel applications of computational approaches in the genomic era. Trends in Biotechnology, 2000. vol. 18, pp. 34-39.*

Burgess, Shaheen, Ravera, Jaye, Donohue, and Winkles. Possible dissociation of the heparin-binding and mitogenic activities of heparin-binding (acidic fibroblast) growth factor-1 from its receptor binding activities by site directed mutagenesis of a single lysine residue. Journal of Cell Biology, 1990. vol. 111, pp. 2129-2138.*

Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*

Rudikoff, Giusti, Cook, and Scharff. Single amino acid substitution altering antigen-binding specificity. Proceedings of the National Academy of Sciences, 1982. vol. 79, pp. 1979-1982.*

Mac Callum, Martin, and Thornton. Antibody-antigen interactions: contact analysis and binding site topography. Journal of Molecular Biology, 1996. vol. 262, pp. 732-745.*

De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*

Holm, Jafari, and Sundstrom. Functional mapping and single chain construction of the anti-cytokeratin 8 monoclonal antibody TS1. Molecular Immunology, 2007. vol. 44, pp. 1075-1084.*

Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*

Wu, Nie, Huse, and Watkins. Humanization of a murine monoclonal antibody by simultaneous optimization of framework and CDR residues. Journal of Molecular Biology, 1999. vol. 294, pp. 151-162.*

Chapman, A.P. et al.; "Therapeutic Antibody Fragments with Prolonged in Vivo Half-Lives"; 1999, *Nature Biotechnology*, vol. 17, No. 8, pp. 780-783. Frank, D.W. et al.; "Generation and Characterization of a Protective Monoclonal Antibody to *Pseudomonas aeruginosa* Perv"; 2002, *Journal of Infectious Diseases*, vol. 186, No. 1, pp. 64-73.

Humphreys, David P. et al.; "Alternative antibody Fab' fragment PEGylation strategies: combination of strong reducing agents, disruption of the interchain disulphide bond and disulphide engineering"; 2007, *Protein Engineering Design & Selection*, vol. 20, No. 5, pp. 227-234.

Knight, David M. et al.; "Pharmacodynamic enhancement of the anti-platelet antibody Fab abciximab by site-specific pegylation"; 2004, *Platelets*, vol. 15, No. 7, pp. 409-418.

* cited by examiner

*Primary Examiner* — Anne M. Gussow

(74) *Attorney, Agent, or Firm* — Kilpatrick Townsend & Stockton LLP

(57) ABSTRACT

The current invention provides high-affinity antibodies to the *Pseudomonas aeruginosa* PcrV protein that have reduced immunogenicity when administered to treat *Pseudomonas aeruginosa* infections.

15 Claims, 7 Drawing Sheets

Figure 1

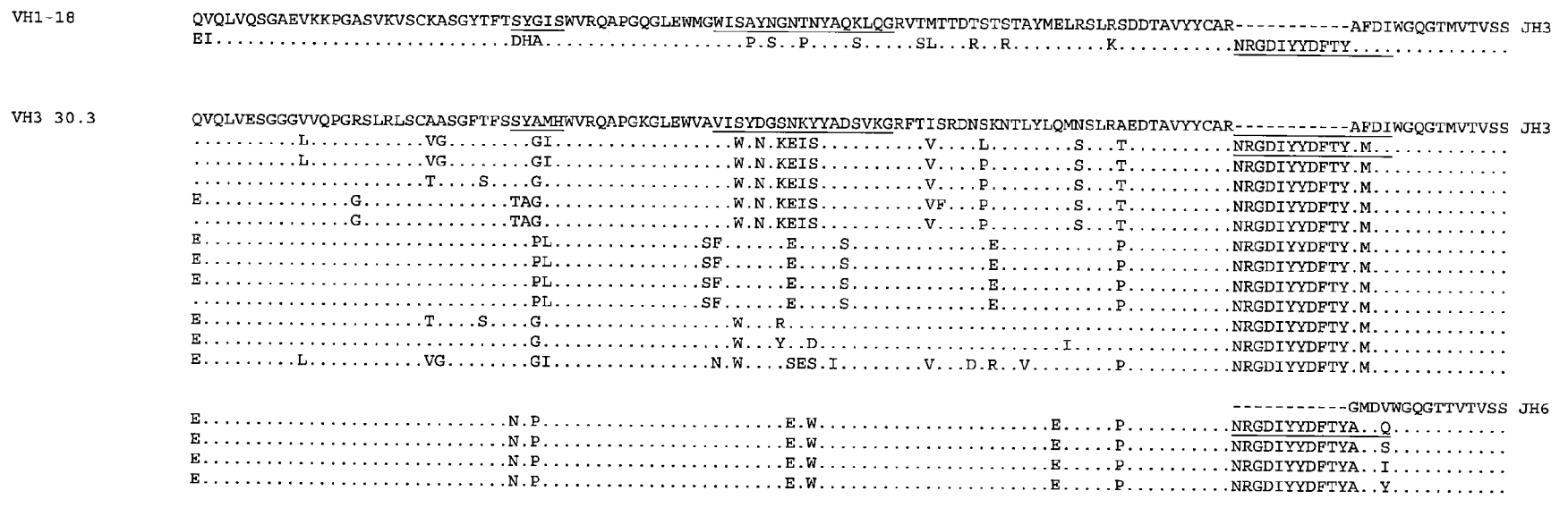

```
VH1-18     QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCAR----------AFDIWGQGTMVTVSS JH3
           EI...........................DHA..................P.S..P....S.....SL...R..R.........K..........NRGDIYYDFTY..............

VH3 30.3   QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCAR----------AFDIWGQGTMVTVSS JH3
           ..........L...........VG........GI.................W.N.KEIS..........V....L........S...T..........NRGDIYYDFTY.M............
           ..........L...........VG........GI.................W.N.KEIS..........V....P........S...T..........NRGDIYYDFTY.M............
           ......................T....S....G..................W.N.KEIS..........V....P........S...T..........NRGDIYYDFTY.M............
           E..............G.............TAG..................W.N.KEIS..........VF...P........S...T..........NRGDIYYDFTY.M............
           ...............G.............TAG..................W.N.KEIS..........V....P........S...T..........NRGDIYYDFTY.M............
           E................................PL.............SF......E....S.............E...........P..........NRGDIYYDFTY.M............
           E................................PL.............SF......E....S.............E...........P..........NRGDIYYDFTY.M............
           E................................PL.............SF......E....S.............E...........P..........NRGDIYYDFTY.M............
           .................................PL.............SF......E....S.............E...........P..........NRGDIYYDFTY.M............
           E.....................T....S....G..................W...R.................................................NRGDIYYDFTY.M............
           E................................G..................W...Y..D......................I...............NRGDIYYDFTY.M............
           E.........L...........VG........GI...............N.W....SES.I.........V...D.R..V.........P..........NRGDIYYDFTY.M............

                                                                                                     ----------GMDVWGQGTTVTVSS JH6
           E............................N.P......................E.W......................E.....P..........NRGDIYYDFTYA..Q..........
           E............................N.P......................E.W......................E.....P..........NRGDIYYDFTYA..S..........
           E............................N.P......................E.W......................E.....P..........NRGDIYYDFTYA..I..........
           E............................N.P......................E.W......................E.....P..........NRGDIYYDFTYA..Y..........
```

FIGURE 2

```
VkI L12     DIQMTQSPSTLSASVGDRVTITCRASQSI-SSWLAWYQQKPGKAPKLLIYDASSLESGVPSRFSGSGSGTEFTLTISSLQPDDFATYYCQQYNSYSYTFGQGTKLEIK Jk2
            ...L............S........EGV-DR.........R.........T.Q...............S.........V......HFWGTP...........
            .........SV...............G.-...........R......A...Q.............G.........E.V.......FW.TP...........
            .........F................G.-.TY......R.......SA...Q.........V..D.........SE..V.....FW.TP...........
            ...L.....F................G.-.TY..................A.Q.......................E.V.......FW.TP...........
            ...L.....F................G.-.TY..................A.Q.......................E.V.......FW.TP...........
            A..L.....F................G.-.TY..............A...Q.............D.........E.V.......FW.TP...........
            .........S..................-.R.V.....R.....N........K.......................E.I.......FW.TP...........
            .........S..................-.R.V.....R.....N........K.......................E.I.......FW.TP...........
            .........S..................-.R.V.....R.....N........K.......................E.I.......FWGTP...........
            ...L............S........EGV-DR.........R.........T.Q...............S.........V......HFW.TP...........

VkIII L2    EIVMTQSPATLSVSPGERATLSCRASQSV-SSNLAWYQQKPGQAPRLLIYGASTRATGIPARFSGSGSGTEFTLTISSLQSEDFAVYYCQQYNNWPYTFGQGTKLEIK Jk2
            ...L..F.G...L............N..GAY...................R..P...D.........D.....NR.EP..........FWST............
            ............................-...........................................................FWST............
            ............................-.................F.A.......................................FWST............
            ............................-...........................................................FWST............

VL3 31      SSELTQDPAVSVALGQTVRITCQGDSLRSYYASWYQQKPGQAPVLVIYGKNNRPSGIPDRFSGSSSGNTASLTITGAQAEDEADYYCNSRDSSGNHVVFGGGTKLTVL J12
            ..........................................................................................QHFW.TP--YT..........
            .................T.........L...............L.S..S.......................R.........QHFW.TP--YT..........

VL2 2c      QSALTQPPSASGSPGQSVTISCTGTSSDVGGYNYVSWYQQHPGKAPKLMIYEVSKRPSGVPDRFSGSKSGNTASLTVSGLQAEDEADYYCSSYAGSNNFVVFGGGTKLTVL J12
            ..V.........................A.........Y...V...I....T........................R.........QHFWSTP--YT..........
            .......A.V.......I.........-----................I..D.TN.....................I............QHFWSTP--YT..........
```

Figure 3

Exemplary heavy chain constant region for an Fd′

ASTKGP SVFPLAPSSK STSGGTAALG CLVKDYFPEP VTVSWNSGAL TSGVHTFPAV
LQSSGLYSLS SVVTVPSSSL GTQTYICNVN HKPSNTKVDK KVEPKSCDKT HTCPPCPA

Exemplary light chain (Kappa) constant region

RTV AAPSVFIFPP SDEQLKSGTA SVVCLLNNFY PREAKVQWKV DNALQSGNSQ
ESVTEQDSKD STYSLSSTLT LSKADYEKHK VYACEVTHQG LSSPVTKSFN RGEC

ANTIBODIES TO THE PCRV ANTIGEN OF *PSEUDOMONAS AERUGINOSA*

CROSS-REFERENCE TO RELATED APPLICATIONS

This application claims benefit of U.S. provisional application No. 60/991,679, filed Nov. 30, 2007, which application is herein incorporated by reference.

BACKGROUND OF THE INVENTION

*Pseudomonas aeruginosa* (*P. aeruginosa*) is an opportunistic pathogen that rarely causes disease in healthy people, but is a significant problem for critically ill or immunocompromised individuals. Infection is a major problem in individuals who have cystic fibrosis (CF), where *P. aeruginosa* is a causative agent in the progressive loss of lung function resulting from recurrent and chronic respiratory tract infections with the bacterium. Others at risk from *Pseudomonas aeruginosa* infection include patients on mechanical ventilators, neutropenic cancer patients, and burn patients. *P. aeruginosa* is often resistant to most antibiotics and new treatment approaches are greatly needed.

The type III secretion system is an important virulence factor determinant in that it inhibits host defense system. Upon activation, the type III secretion apparatus translocates toxins into the cytoplasm of the host cell, resulting in cell rounding, lifting, and cell death by necrosis or apoptosis. PcrV is an essential component of the type III secretion apparatus. Blocking of PcrV can inhibit toxin secretion through the Type III secretion system, thereby allowing natural clearance mechanisms to eliminate the bacteria. PcrV is conserved in all *P. aeruginosa* strains tested thus far.

Antibodies to the PcrV antigen of *Pseudomonas* are known in the art. The current invention provides improved PcrV antibodies, e.g., for the treatment of *Pseudomonas aeruginosa* infections.

BRIEF SUMMARY OF THE INVENTION

The current invention relates to engineered antibodies that bind with high affinity, e.g., at about 50 nM, or about 10 nM or less, to the PcrV antigen from *Pseudomonas aeruginosa*. Such antibodies are often functional antagonists of the Type III secretion, i.e., the antibody binds to PcrV and inhibits the Type III secretion system. In some embodiments, an antibody of the invention may bind to PcrV and recruit multiple cell types of the immune system to stimulate phagocytosis by macrophages, antibody directed cellular cytotoxicity (ADCC) by macrophages or NK cells, activation of the complement cascade, and/or generation of the oxidative burst by neutrophils.

The antibodies of the invention have variable regions with a high degree of identity to human germ-line $V_H$ and $V_L$ sequences and are less immunogenic in humans. The CDR3 sequences of the heavy and light chains of the present invention comprise a pair of binding specificity determinants (BSD) from the monoclonal anti-PcrV antibody Mab166 (Frank et al., *J. Infectious Dis.* 186: 64-73, 2002). The antibodies of the invention typically are capable of competing with Mab166 for binding to a neutralizing epitope on the PcrV protein.

The BSD sequence in CDRH3 has the amino acid sequence NRGDIYYDFTY (SEQ ID NO:38). The BSD in CDRL3 is FWXTP (where X may be either S or G; SEQ ID NO:39). Complete V-regions are generated in which the BSD forms part of the CDR3 and additional sequences are used to complete the CDR3 and add a FR4 sequence. Typically, the portion of the CDR3 excluding the BSD and the complete FR4 are comprised of human germ-line sequences. Preferably, the CDR3-FR4 sequence excluding the BSD differs from human germ-line sequences by not more than two amino acids on each chain. The CDR3-FR4 is joined to a V-segment that has a high degree identity, e.g., at least 80%, or at least 90%, or more to a human germline V segment.

In some aspects, the invention provides an anti-PcrV antibody that exhibits high affinity binding, e.g., 10 nM or better, to PcrV and is an antagonist of the Type III secretion system.

In many embodiments, an anti-PcrV antibody of the invention that selectively binds to PcrV comprises: a $V_L$ region that comprises a CDR3 comprising FWGTP (SEQ ID NO:40). In typical embodiments, such an antibody has a $V_L$ region V-segment has at least 80% identity to a human germline V-segment. The FR4 region typically has at least 90% identity to the FR4 region of a human germline J segment.

In some embodiments, an anti-PcrV antibody of the invention comprises a CDR3 comprising FWGTP (SEQ ID NO:40), a FR4 and a V-segment, wherein the FR4 comprises at least 90% identity to the FR4 region of the human JK2 germline gene segment or at least 90% identity to the JL2 germline sequence; and the V-segment comprises at least 80% identity to a human germline Vkappa I or Vkappa III sequence, or at least 80% identity to a human germline Vlambda sequence. In some embodiments the $V_L$ region CDR3 has the sequence Q(Q/H)FWGTPYT (SEQ ID NO:41). In some embodiments, the antibody further comprises a $V_H$ region that comprises a CDR3 having a sequence NRGDIYYDFTY (SEQ ID NO:38), a FR4 and a V-segment, wherein the FR4 comprises at least 90% identity to the FR4 region of the human JH3 or human JH6 segment and the V-segment comprises at least 80% identity to the human VH1-18 subclass V-segment or to the human VH3-30.3 V segment. In some embodiments, the $V_H$ region comprises a CDR3 having a sequence NRGDIYYDFTYA(M/F)D$X_1$ (SEQ ID NO:42), wherein $X_1$ is I, Q, Y, or S.

In further embodiments, the invention provides an anti-PcrV antibody that binds to PcrV, comprising: a $V_H$ region that comprises a CDR3 having a sequence NRGDIYYDFTYAMD$X_1$ (SEQ ID NO:43), wherein $X_1$ is I, Q, Y, or S; a FR4 and a V-segment, wherein the FR4 comprises at least 90% identity to the FR4 region of the human germline JH3 segment or the FR4 region of the human germine JH6 segment, and the V-segment comprises at least 80% identity to the human germline VH1-18 subclass V-segment or to the human germline VH3-30.3 subclass V segment, with the proviso that when $X_1$ is Y, the FR4 region is not WGQGTSVTVSS (SEQ ID NO:44).

In some embodiments, the invention provides an anti-PcrV antibody that binds to PcrV, comprising: a $V_H$ region that comprises a CDR3 having a sequence NRGDIYYDFTYAMD$X_1$ (SEQ ID NO:43), wherein $X_1$ is I, Q, Y, or S; a FR4 and a V-segment, wherein the FR4 comprises at least 90% identity to the FR4 region of the human germline JH3 segment or the FR4 region of the human germline JH6 segment, and the V-segment comprises at least 80% identity to the human germline VH1-18 subclass V-segment or to the human germline VH3-30.3 subclass V segment, with the proviso that when $X_1$ is Y, the FR4 region is not WGQGTSVTVSS (SEQ ID NO:44); and a $V_L$ region that comprises a CDR3 comprising FW(S/G)TP (SEQ ID NO:39), a FR4 and a V-segment, wherein the FR4 comprises at least 90% identity to the FR4 region of the human germline JK2 gene segment or to the FR4 region of the human germline JL2 segment; and the V-segment comprises at least 80% identity to the human germline VKI L12 sequence, or at least 80% identity to a Vkappa III sequence, or at least 80% identity to a human germline Vlambda2 2c or Vlambda3 31 segment.

In some embodiment, the FR4 of the $V_H$ region of an antibody of the invention has the sequence WGQGTX$_2$VTVSS (SEQ ID NO:45), wherein X$_2$ is T or M.

In some embodiments, an antibody of the invention has a light chain CDR3 that has the sequence Q(H/Q)FW(G/S)TPYT (SEQ ID NO:46).

In some embodiments, the FR4 of the $V_L$ region has the sequence FGQGTKLEIK (SEQ ID NO:47) or FGGGTKLTVL (SEQ ID NO:48).

The invention also provides an anti-PcrV antibody where the $V_H$ region V-segment has at least 80% identity to the human germline VH3-3.0.3 segment and the heavy chain region CDR1 comprises the sequence X$_3$X$_4$X$_5$X$_6$H, wherein X$_3$ is S, T, or N; X$_4$ is Y or A; X$_5$ is A, G, or P; and X$_6$ is M, I, or L; and the heavy chain region CDR2 comprises the sequence X$_7$IX$_8$YX$_9$GX$_{10}$X$_{11}$X$_{12}$X$_{13}$Y(A/I)X$_{14}$SVKG (SEQ ID NO:49), wherein X$_7$ is V, F, or N; X$_8$ is S or W; X$_9$ is D or N; X$_{10}$ is S, K, R or Y; X$_{11}$ is N, S, D or E; X$_{12}$ is K, I, or E; X$_{13}$ is Y, S, D or W; and X$_{14}$ is D or S. In some embodiments, the antibody has at least 90% identity to a VH3-30.3 V segment. In some embodiments, the CDR1 is TAGMH (SEQ ID NO:50), SYGIH (SEQ ID NO:51), SYGMH (SEQ ID NO:52), SYPLH (SEQ ID NO:53), or NYPMH (SEQ ID NO:54). In some embodiments, the CDR2 is VIWYNGKEISYADSVKG (SEQ ID NO:55), FISYDGSEKYYASSVKG (SEQ ID NO:56), VISYDGSEKWYADSVKG (SEQ ID NO:57), VIWYDGRNKYYADSVKG (SEQ ID NO:58), VIWYDGYNKDYADSVKG (SEQ ID NO:59), or NIWYDGSSESYIDSVKG (SEQ ID NO:60). In some embodiments, the CDR1 is TAGMH (SEQ ID NO:50), SYGIH (SEQ ID NO:51), SYGMH (SEQ ID NO:52), SYPLH (SEQ ID NO:53), or NYPMH (SEQ ID NO:54); and the CDR2 is VIWYNGKEISYADSVKG (SEQ ID NO:55), FISYDGSEKYYASSVKG (SEQ ID NO:56), VISYDGSEKWYADSVKG (SEQ ID NO:57), VIWYDGRNKYYADSVKG (SEQ ID NO:58), VIWYDGYNKDYADSVKG (SEQ ID NO:59), or NIWYDGSSESYIDSVKG (SEQ ID NO:60).

The invention also provides an anti-PcrV antibody where the $V_H$ region V-segment has at least 80% identity, or at least 90% identity, to the human germline VH1-18 sub-class V-segment and the CDR1 has the sequence DHAIS (SEQ ID NO:61) and the CDR2 has the sequence WISPYSGNPNYAQSLQG (SEQ ID NO:62).

The invention also provides an anti-PcrV antibody where the $V_H$ region V-segment has at least 80% identity, or at least 90% identity, to the human germline VH1-18 sub-class V-segment and the CDR1 has the sequence DHAIS and the CDR2 has the sequence WISPYSGNPNYAQSLQG.

The invention also provides an anti-PcrV antibody that binds to PcrV, comprising: a VH region that has a CDR3 sequence NRGDIYYDFTYAFDI (SEQ ID NO:63), a CDR1 sequence DHAIS (SEQ ID NO:61) and a CDR2 sequence WISPYSGNPNYAQSLQG (SEQ ID NO:62).

In some embodiments the $V_H$ region comprises the V-segment region of an amino acid sequence selected from the group consisting of SEQ ID NOS:1, 3, 5, 7, 9, 11, 13, 15, 17, 19, 21, 23, 25, 26, 27, 29, and 35. For example, the $V_H$ regions can comprise an amino acid sequence selected from the group consisting of SEQ ID NOS:1, 3, 5, 7, 9, 11, 13, 15, 17, 19, 21, 23, 25, 26, 27, 29, and 35.

The invention also provides an anti-PcrV where the $V_L$ region V-segment comprises at least 80% or 90% identity, to a human germline Vkappa 1 L12 or Vkappa III sequence; or at least 80% or 90% identity to a human germline Vlambda3 31 or to a Vlambda2 2c sequence. In some embodiments, $V_L$ region V-segment has at least 80% or 90% identity to the human germline VKI L12 segment and the CDR1 has the sequence RASX$_{15}$X$_{16}$X$_{17}$X$_{18}$X$_{19}$X$_{20}$X$_{21}$A (SEQ ID NO:64), where X$_{15}$ is Q or E; X$_{16}$ is S or G; X$_{17}$ is I or V; X$_{18}$ is S or D; X$_{19}$ is S, R, or T; X$_{20}$ is W or Y; and X$_{21}$ is L or V; and the CDR2 has the sequence X$_{21}$ASX$_{22}$LX$_{23}$S (SEQ ID NO:65), wherein X$_{21}$ is D or A; X$_{22}$ is S, A, or T; and X$_{23}$ is E, Q, or K. In some embodiments, the CDR1 has the sequence RASQGISTYLA (SEQ ID NO:66), RASQGISSWLA (SEQ ID NO:67), RASQSISRWVA (SEQ ID NO:68), or RASEGVDRWLA (SEQ ID NO:69); or the CDR2 has the sequence AASSLQS (SEQ ID NO:70), DASSLKS (SEQ ID NO:71), DASALQS (SEQ ID NO:72), or DASTLQS (SEQ ID NO:73). In some embodiments, the CDR1 has the sequence RASQGISTYLA (SEQ ID NO:66), RASQGISSWLA (SEQ ID NO:67), RASQSISRWVA (SEQ ID NO:68), or RASEGVDRWLA (SEQ ID NO:69); and the CDR2 has the sequence AASSLQS (SEQ ID NO:70), DASSLKS (SEQ ID NO:71), AASSLQS, DASALQS (SEQ ID NO:72), or DASTLQS (SEQ ID NO:73).

The invention also provides an anti-PcrV antibody where the $V_L$ region V segment has at least 80%, or at least 90%, amino acid sequence identity to the human germline VKIII L2 sequence and the CDR1 has the sequence RASNSVGAYNLA (SEQ ID NO:74) or RASQSVSSNLA (SEQ ID NO:75); or the CDR2 has the sequence (A/G)AS(T/R)RA(T/P) (SEQ ID NO:76). In some embodiments, CDR1 has the sequence RASNSVGAYNLA (SEQ ID NO:74) or RASQSVSSNLA (SEQ ID NO:75); and the CDR2 has the sequence (A/G)AS(T/R)RA(T/P) (SEQ ID NO:76).

Further, the invention provides an anti-PcrV antibody where the $V_L$ region V-segment has at least 80%, or at least 90%, amino acid sequence identity to a human germline Vlambda L3 31 segment and the CDR1 has the sequence QGDSLRS(Y/L)YAS (SEQ ID NO:77); or the CDR2 has the sequence (G/S)KN(N/S)RPS (SEQ ID NO:78). In some embodiments, the CDR1 has the sequence QGDSLRS(Y/L)YAS (SEQ ID NO:77); and the CDR2 has the sequence (G/S)KN(N/S)RPS (SEQ ID NO:78).

In some embodiments, the invention provide an anti-PcrV antibody where the $V_L$ region V-segment has at least 80%, or at least 90%, amino acid sequence identity to a human germline Vlambda L2 2c segment and the CDR1 has the sequence TGTSSDVGAYNYVS (SEQ ID NO:79) or TGTSSDYVS (SEQ ID NO:80); or the CDR2 has the sequence (E/D)VT(K/N)RPS (SEQ ID NO:81). In some embodiments, the CDR1 has the sequence TGTSSDVGAYNYVS (SEQ ID NO:79) or TGTSSDYVS (SEQ ID NO:80); and the CDR2 has the sequence (E/D)VT(K/N)RPS (SEQ ID NO:81).

An anti-PcrV antibody of the invention can have a region that comprises the V-segment of an amino acid sequence selected from the group consisting of SEQ ID NO:2, 4, 6, 8, 10, 12, 14, 16, 18, 20, 22, 24, 28, 30, 32, 34, 36, and 37. For example the $V_L$ region can comprise an amino acid sequence selected from the group consisting of SEQ ID NO:2, 4, 6, 8, 10, 12, 14, 16, 18, 20, 22, 24, 28, 30, 32, 34, 36, and 37.

The invention thus provides an anti-PcrV antibody that comprises: a $V_H$ region having an amino acid sequence selected from the group consisting of SEQ ID NOS:1, 3, 5, 7, 9, 11, 13, 15, 17, 19, 21, 23, 25, 26, 27, 29, and 35; and a $V_L$ region having an amino acid sequence selected from the group consisting of SEQ ID NO:2, 4, 6, 8, 10, 12, 14, 16, 18, 20, 22, 24, 28, 30, 32, 34, 36, and 37. Thus, in some embodiments, an antibody of the invention comprises a $V_H$ region of SEQ ID NO:1 and a $V_L$ region of SEQ ID NO:2; or a $V_H$ region of SEQ ID NO:3 and a $V_L$ region of SEQ ID NO:4; or a $V_H$ region of SEQ ID NO:5 and a $V_L$ region of SEQ ID NO:6; or a $V_H$ region of SEQ ID NO:7 and a $V_L$ region of SEQ ID NO:8; or a $V_H$ region of SEQ ID NO:11 and a $V_L$ region of SEQ ID NO:12; or a $V_H$ region of SEQ ID NO:9 and a $V_L$ region of SEQ ID NO:10; or a $V_H$ region of SEQ ID NO:13 and a $V_L$ region of SEQ ID NO:10; or a $V_H$ region of SEQ ID NO:13 and a $V_L$ region of SEQ ID NO:4; or a $V_H$ region of SEQ ID NO:13 and a $V_L$ region of SEQ ID NO:37; or a $V_H$ region of SEQ ID NO:21 and a $V_L$ region of SEQ ID NO:18; or a $V_H$ region of SEQ ID NO:17 and a $V_L$ region of SEQ ID NO:18; or a $V_H$ region of SEQ ID NO:26 and a $V_L$ region of SEQ ID NO:24; or a $V_H$ region of SEQ ID NO:25 and a $V_L$ region of SEQ ID NO:24; or a $V_H$ region of SEQ ID NO:23 and a $V_L$ region of SEQ ID NO:24; or a $V_H$ region of SEQ ID NO:35 and a $V_L$ region of SEQ ID NO:36; or $V_H$ region of SEQ ID NO:29 and a $V_L$ region of SEQ ID NO:20; or $V_H$ region of SEQ ID NO:29 and a $V_L$ region of SEQ ID NO:28; or a $V_H$ region of SEQ ID NO:29 and a $V_L$ region of SEQ ID NO:30; or a $V_H$ region of SEQ ID NO:29 and a $V_L$ region of SEQ ID NO:34; or a $V_H$ region of SEQ ID NO:3 and a $V_L$ region of SEQ ID NO:32.

In some embodiments, an anti-PcrV antibody of the invention comprises a heavy chain as set forth in FIG. 1 and/or a light chain as set forth in FIG. 2; or has at least one, often at least two, and in some embodiments, at least three CDRs from one of the heavy or light chains set forth in FIG. 1 or FIG. 2, respectively. In many embodiments, the CDR1 and/or CDR2 sequence is not a germline sequence.

In some embodiments, the antibody is a Fab' fragment.

In some embodiments, an antibody of the invention is a Fab, or Fab', that has an affinity of about 10 nM or less. In some embodiments, the antibody has an affinity that is equal or better than, the affinity of a Mab166 Fab or Fab'.

The potency of an antibody of the invention, e.g., a Fab, in inhibiting the activity of the *P. aeruginosa* Type III Secretion System is typically equivalent to Mab 166 Fab (within two-fold of the activity in cell-based assays). In some embodiments, an antibody of the invention is more potent than Mab 166 in preventing cytotoxicity by *P. aeruginosa*.

In some embodiments, the antibody comprises a hinge region.

In other embodiments, the antibody is an IgG or an IgA.

In some embodiments, the antibody is PEGylated. For example, the antibody can be di-PEGylated.

In some embodiments, the $V_H$ region or the $V_L$ region, or both the $V_H$ and $V_L$ region amino acid sequences comprise a methionine at the N-terminus.

In a further aspect, the invention provides a method of treating a patient infected with *P. aeruginosa*, the method comprising administering a therapeutically effective amount of an antibody as described herein. In some embodiments, the antibody is administered intravenously, subcutaneously, or by insufflation.

BRIEF DESCRIPTION OF THE DRAWINGS

FIG. 1 shows sequences of $V_H$ regions of anti-PcrV antibodies (SEQ ID NOS:1, 7, 9, 5, 11, 3, 19, 19, 19, 13, 15, 17, 21, 23, 25, 26 and 35, respectively). CDR sequences are underlined. The VH1 sequence is aligned to human germ-line sequence VH1-18 (SEQ ID NO:82). VH3-subclass antibodies are shown aligned to human germ-line sequence VH3-30.3 (SEQ ID NO:83). J-segments are aligned to either human germ-line JH3 or JH6 (SEQ ID NO:84). The $V_H$-segments depicted in FIG. 1 correspond to the sequence up to the CDR3 sequence.

FIG. 2 shows sequences of $V_L$ regions of anti-PcrV antibodies (SEQ ID NOS:24, 2, 8, 10, 10, 6, 12, 4, 37, 36, 87, 18, 20, 18, 30, 32, 90 and 28, respectively). CDR sequences are underlined. Vkappa-subclass antibodies are shown aligned to human germline sequence VkI L12 (SEQ ID NO:85) or VkIII L2 (SEQ ID NO:86). J-segments are aligned to human germline Jk2. Vlambda-subclass antibodies are shown aligned to human germline sequence VL3 31 (SEQ ID NO:88) or VL2 2c (SEQ ID NO:89). J-segments are aligned to human germline J12.

FIG. 3 shows an exemplary constant region sequence that can be linked to Fab' Heavy (SEQ ID NO:91) and Light (SEQ ID NO:92) Chains. The two cysteine residues in the hinge region available for conjugation of thiol-reactive maleimide derivatives are underlined. The cysteine residues involved in formation of an interchain disulfide bond are boxed.

DETAILED DESCRIPTION OF THE INVENTION

Figure 4:
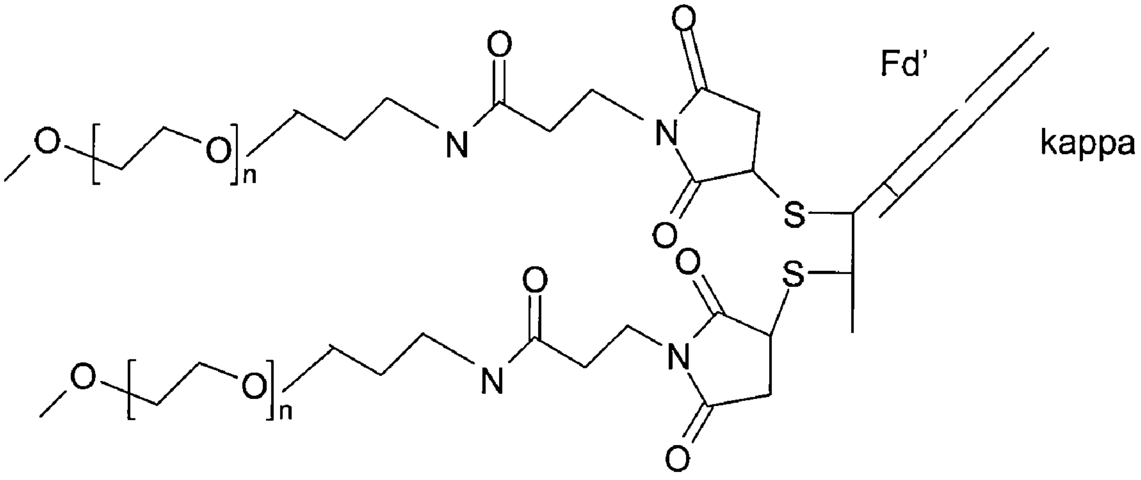
FIG. 4 shows a schematic representation of the structure of a di-PEGylated Fab' in which two molecules of mPEG-maleimide are conjugated via thioether linkages to cysteine residues in the hinge region of the Fab' protein. The exemplary antibody is comprised of a human Fd' heavy chain and human kappa light chain linked by a disulphide bond represented by the cross-bar between the two chains. (Fab and PEG components are not to scale.)
Figure 5A:
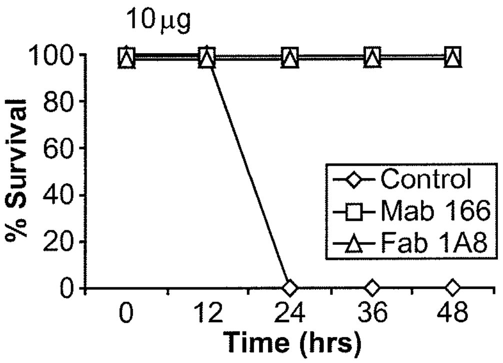
FIG. 5 provides data showing a time course of survival of mice treated with various doses of antibodies to PcrV at the time of challenge with a lethal dose of PA103. Mab166 and Fab fragments were co-instilled via the intratracheal route with 1.5×106 bacteria (5 mice per group, 4 mice for Mab166 Fab groups). Control is a nonspecific Fab with no binding to PcrV or any *P. aeruginosa* protein. Mice were treated with antibody doses of: A) 10 μg, B) 5 μg, C) 2.5 μg, D) 1.25 μg, *P=0.01 for Fab 1A8 vs. Mab166 Fab E) 0.625 μg *P=0.002 for 1A8 vs. Mab166 Fab, F) 0.3125 μg, G) 0.16 μg, H) 0.08 μg. P values for differences between treatment groups determined by Mantel-Cox log-rank test.
Figure 5B:
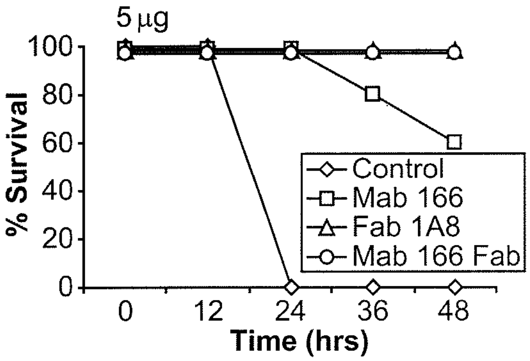
Figure 5C:
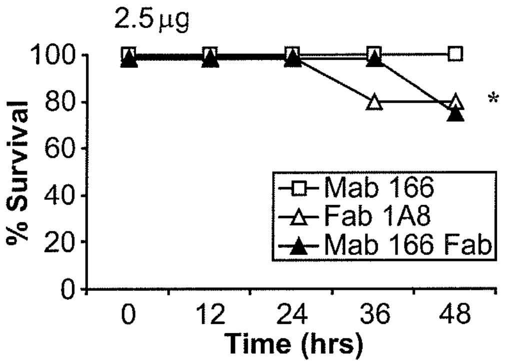
Figure 5D:
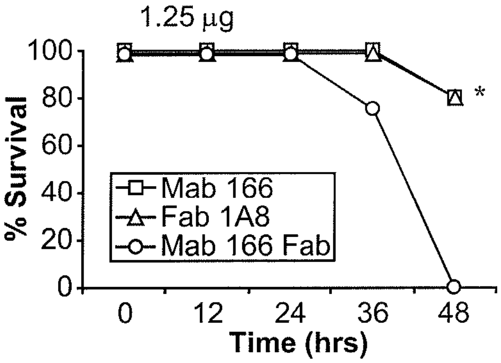
Figure 5E:
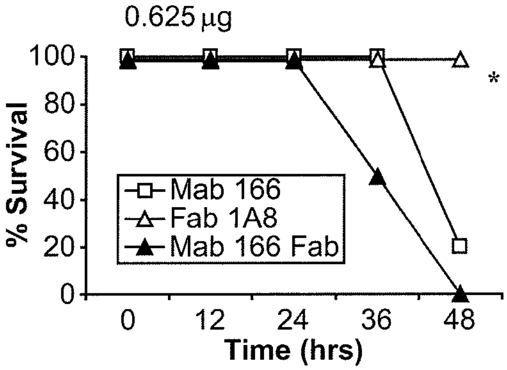
Figure 5F:
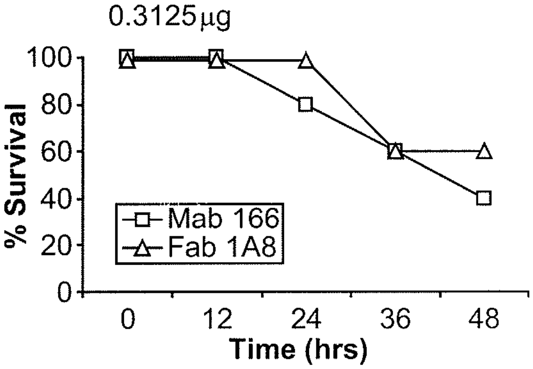
Figure 5G:
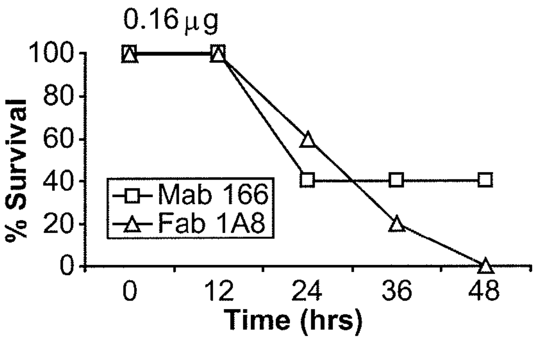
Figure 5H:
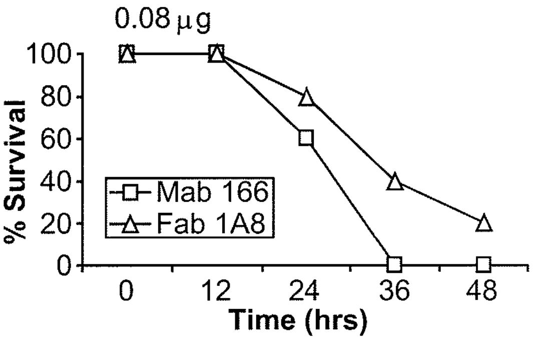
Figure 6A:
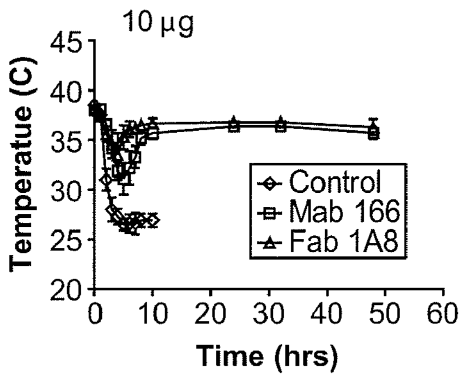
FIG. 6 provides data showing a body temperature analysis of mice treated with anti-PcrV antibodies. Rectal temperatures are shown for 48 hours or until mortality. Antibody doses: A) 10 μg, B) 5 μg, C) 2.5 μg, D) 1.25 μg E) 0.625 μg F) 0.3125 μg, G) 0.16 μg, H) 0.08 μg.
Figure 6B:
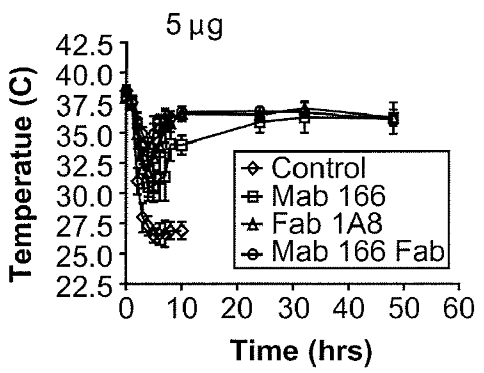
Figure 6C:
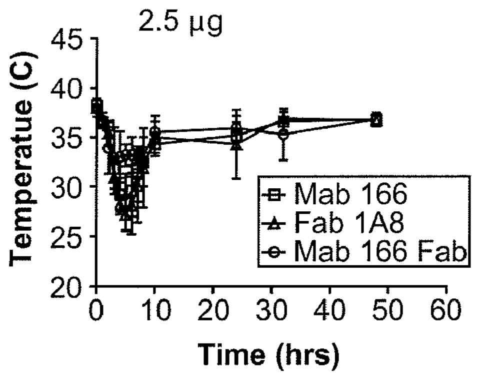
Figure 6D:
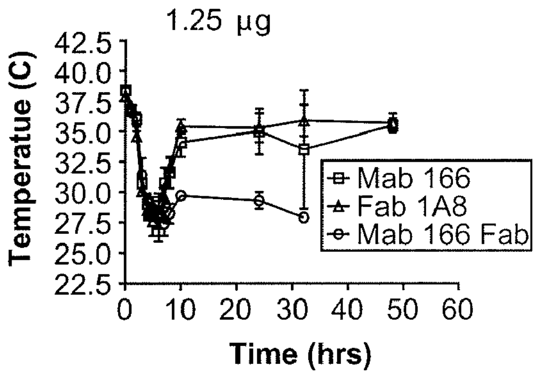
Figure 6E:
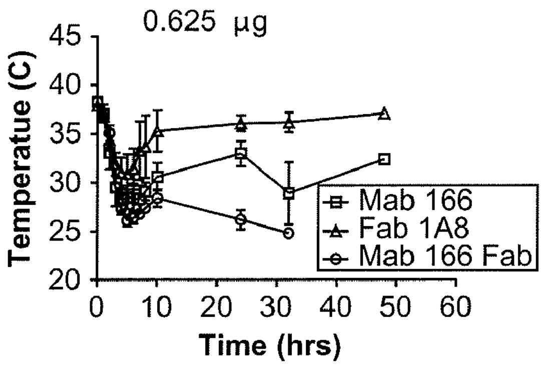
Figure 6F:
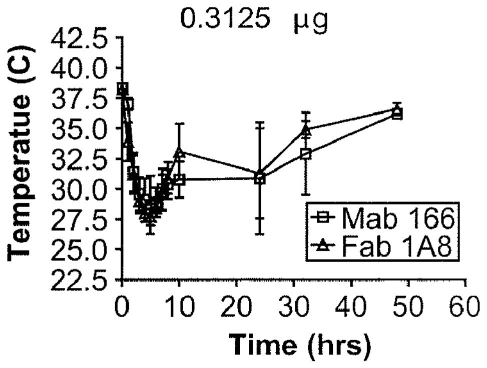

As used herein, an "antibody" refers to a protein functionally defined as a binding protein and structurally defined as comprising an amino acid sequence that is recognized by one of skill as being derived from the framework region of an immunoglobulin-encoding gene of an animal that produces antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

The term "antibody" as used herein includes antibody fragments that retain binding specificity. For example, there are a number of well characterized antibody fragments. Thus, for example, pepsin digests an antibody below the disulfide linkages in the hinge region to produce $F(ab)'_2$, a dimer of Fab which itself is a light chain joined to VH—CH1 (Fd) by a disulfide bond. The $F(ab)'_2$ may be reduced under mild conditions to break the disulfide linkage in the hinge region thereby converting the $(Fab')_2$ dimer into an Fab' monomer. The Fab' monomer is essentially a Fab with all or part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody, as used herein also includes antibody fragments either produced by the modification of whole antibodies or synthesized using recombinant DNA methodologies.

Antibodies of the invention include dimers such as $V_H$-$V_L$ dimers, $V_H$ dimers, or $V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker (e.g., Huston, et al. *Proc. Nat. Acad. Sci. USA,* 85:5879-5883, 1988). While the $V_H$ and $V_L$ are connected to each as a single polypeptide chain, the $V_H$ and $V_L$ domains associate non-covalently. Alternatively, the antibody can be another fragment, such as a disulfide-stabilized Fv (dsFv). Other fragments can also be generated, including using recombinant techniques. The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). In some embodiments, antibodies include those that have been displayed on phage or generated by recombinant technology using vectors where the chains are secreted as soluble proteins, e.g., scFv, Fv, Fab, $(Fab')_2$ or generated by recombinant technology using vectors where the chains are secreted as soluble proteins. Antibodies for use in the invention can also include diantibodies and miniantibodies.

Antibodies of the invention also include heavy chain dimers, such as antibodies from camelids. Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called VHH domains. Antibodies of the invention include single domain antibodies (dAbs) and nanobodies (see, e.g., Cortez-Retamozo, et al., *Cancer Res.* 64:2853-2857, 2004).

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation. A "V-segment" as used herein refers to the region of the V-region (heavy or light chain) that is encoded by a V gene. The V-segment of the heavy chain variable region encodes FR1-CDR1-FR2-CDR2 and FR3. For the purposes of this invention, the V-segment of the light chain variable region is defined as extending though FR3 up to CDR3.

As used herein, the term "J-segment" refers to a subsequence of the variable region encoded comprising a C-terminal portion of a CDR3 and the FR4. An endogenous J-segment is encoded by an immunoglobulin J-gene.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, for example, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. *J. Mol. Biol.* 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., *J. Mol. Biol.* 1997, 273(4)). Definitions of antigen combining sites are also described in the following: Ruiz et al., IMGT, the international ImMunoGeneTics database. *Nucleic Acids Res.,* 28, 219-221 (2000); and Lefranc, M.-P. IMGT, the international ImMunoGeneTics database. *Nucleic Acids Res.* January 1; 29(1):207-9 (2001); MacCallum et al, Antibody-antigen interactions: Contact analysis and binding site topography, *J. Mol. Biol.,* 262 (5), 732-745 (1996); and Martin et al, *Proc. Natl. Acad. Sci. USA,* 86, 9268-9272 (1989); Martin, et al, *Methods Enzymol.,* 203, 121-153, (1991); Pedersen et al, *Immunomethods,* 1, 126, (1992); and Rees et al, In Sternberg M. J. E. (ed.), Protein Structure Prediction. Oxford University Press, Oxford, 141-172 1996).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The term "binding specificity determinant" or "BSD" as used in the context of the current invention refers to the minimum contiguous or non-contiguous amino acid sequence within a CDR region necessary for determining the binding specificity of an antibody. In the current invention, the minimum binding specificity determinants reside within a portion or the full-length of the CDR3 sequences of the heavy and light chains of the antibody.

As used herein, the terms "PcrV antagonizing antibody" or an "anti-PcrV antibody is an antagonist of the *Pseudomonas aeruginosa* Type III secretion system" are used interchangeably to refer to an antibody that binds to PcrV and inhibits the Type III secretion system. Inhibition occurs when secretion through the Type III secretion system is at least about 10% less, for example, at least about 25%, 50%, 75% less, or totally inhibited, in comparison to secretion when not exposed to the antibody antagonist. The terms "anti-PcrV antibody" and "PcrV antibody" are used synonymously unless otherewise stated.

The term "equilibrium dissociation constant ($K_D$) refers to the dissociation rate constant ($k_d$, time$^{-1}$) divided by the association rate constant ($k_a$, time$_{-1}$, $M^{-1}$). Equilibrium dissociation constants can be measured using any known method in the art. The antibodies of the present invention are high affinity antibodies. Such antibodies have an affinity better than 500 nM, and often better than 50 nM or 10 nM. Thus, in some embodiments, the antibodies of the invention have an affinity in the range of 500 nM to 100 pM, or in the range of 50 or 25 nM to 100 pM, or in the range of 50 or 25 nM to 50 pM, or in the range of 50 nM or 25 nM to 1 pM.

As used herein, "humanized antibody" refers to an immunoglobulin molecule in CDRs from a donor antibody are grafted onto human framework sequences. Humanized antibodies may also comprise residues of donor origin in the framework sequences. The humanized antibody can also comprise at least a portion of a human immunoglobulin constant region. Humanized antibodies may also comprise residues which are found neither in the recipient antibody nor in the imported CDR or framework sequences. Humanization can be performed using methods known in the art (e.g., Jones et al., *Nature* 321:522-525; 1986; Riechmann et al., *Nature* 332:323-327, 1988; Verhoeyen et al., *Science* 239:1534-1536, 1988); Presta, *Curr. Op. Struct. Biol.* 2:593-596, 1992; U.S. Pat. No. 4,816,567), including techniques such as "superhumanizing" antibodies (Tan et al., *J. Immunol.* 169: 1119, 2002) and "resurfacing" (e.g., Staelens et al., *Mol. Immunol.* 43: 1243, 2006; and Roguska et al., *Proc. Natl. Acad. Sci. USA* 91: 969, 1994).

A "humaneered" antibody in the context of this invention refers to an engineered human antibody having a binding specificity of a reference antibody. A "humaneered" antibody for use in this invention has an immunoglobulin molecule that contains minimal sequence derived from a donor immunoglobulin. Typically, an antibody is "humaneered" by joining a DNA sequence encoding a binding specificity determinant (BSD) from the CDR3 region of the heavy chain of the reference antibody to human $V_H$ segment sequence and a light chain CDR3BSD from the reference antibody to a human $V_L$ segment sequence. A "BSD" refers to a CDR3-FR4 region, or a portion of this region that mediates binding specificity. A binding specificity determinant therefore can be a CDR3-FR4, a CDR3, a minimal essential binding specificity determinant of a CDR3 (which refers to any region smaller than the CDR3 that confers binding specificity when present in the V region of an antibody), the D segment (with regard to a heavy chain region), or other regions of CDR3-FR4 that confer the binding specificity of a reference antibody. Methods for humaneering are provided in US patent application publication no. 20050255552 and US patent application publication no. 20060134098.

The term "hybrid" when used with reference to portions of a nucleic acid or protein, indicates that the nucleic acid or protein comprises two or more subsequences that are not normally found in the same relationship to each other in nature. For instance, the nucleic acid is typically recombinantly produced, having two or more sequences, e.g., from unrelated genes arranged to make a new functional nucleic acid. Similarly, a hybrid protein refers to two or more subsequences that are not normally found in the same relationship to each other in nature.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The phrase "specifically (or selectively) binds" to an antibody or "specifically (or selectively) immunoreactive with," when referring to a protein or peptide, refers to a binding reaction where the antibody binds to the protein of interest. In the context of this invention, the antibody typically binds to PcrV with an affinity of 500 nM or less, and has an affinity of 5000 nM or greater, for other antigens.

The terms "identical" or percent "identity," in the context of two or more polypeptide (or nucleic acid) sequences, refer to two or more sequences or subsequences that are the same or have a specified percentage of amino acid residues (or nucleotides) that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." "Substantially identical" sequences also includes sequences that have deletions and/or additions, as well as those that have substitutions, as well as naturally occurring, e.g., polymorphic or allelic variants, and man-made variants. As described below, the preferred algorithms can account for gaps and the like. Preferably, protein sequence identity exists over a region that is at least about 25 amino acids in length, or more preferably over a region that is 50-100 amino acids in length, or over the length of a protein.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" in some embodiments denotes that a protein gives rise to essentially one band in an electrophoretic gel. Preferably, it means that the protein is at least 85% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables and substitution matrices such as BLOSUM providing functionally similar amino acids are well known in the art. Such conservatively modified variants are in addition to and do not exclude polymorphic variants, interspecies homologs, and alleles of the invention. Typical conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

I. Introduction

The invention relates to antibodies that bind with high affinity to the PcrV antigen from *Pseudomonas aeruginosa* and are typically functional antagonists of the Type III secretion system. The antibodies comprise variable regions with a high degree of homology to human germ-line $V_H$ and $V_L$ sequences. The CDR3 sequences of the heavy and light chains comprise a pair of binding specificity determinants (BSD) from the monoclonal anti-PcrV antibody Mab166 (Frank et al., *J Infectious Dis.* 186: 64-73, 2002; and U.S. Pat. No. 6,827,935) and the antibodies of the invention compete with Mab166 for binding to a neutralizing epitope on the PcrV protein (see, e.g., U.S. Pat. No. 6,827,935).

The BSD sequence in CDRH3 has the amino acid sequence NRGDIYYDFTY (SEQ ID NO:38. In some embodiments, an antibody of the invention as a heavy chain CDR3 sequence NRGDIYYDFTYA(M/F)DX (SEQ ID NO:93), where X is I, S, or Q.

The BSD in CDRL3 is FWXTP (where X may be either S or G; SEQ ID NO:39). Complete V-regions are generated in which the BSD forms part of the CDR3 and additional sequences are used to complete the CDR3 and add a FR4 sequence. Typically, the portion of the CDR3 excluding the BSD and the complete FR4 are comprised of human germ-line sequences. In preferred embodiments, the CDR3-FR4 sequence excluding the BSD differs from human germ-line sequences by not more than 2 amino acids on each chain.

The human germline V-segment repertoire consists of 51 heavy chain V-segments, 40 κ light chain V-segments, and 31λ light chain V-segments, making a total of 3,621 germline V-region pairs. In addition, there are stable allelic variants for most of these V-segments, but the contribution of these variants to the structural diversity of the germline repertoire is limited. The sequences of all human germ-line V-segment genes are known and can be accessed in the V-base database (on the worldwide web at vbase.mrc-cpe.cam.ac.uk), provided by the MRC Centre for Protein Engineering, Cambridge, United Kingdom (see, also Chothia et al., 1992, *J Mol Biol* 227:776-798; Tomlinson et al., 1995, *EMBO J* 14:4628-4638; Cook et al. (1995) *Immunol. Today* 16: 237-242 and Williams et al., 1996, *J Mol Biol* 264:220-232); or the international ImMunoGeneTics database (IMGT). These sequences can be used as reference sources for the human germline segments of the antibodies of the invention.

Antibodies or antibodies fragments as described herein can be expressed in prokaryotic or eukaryotic microbial systems or in the cells of higher eukaryotes such as mammalian cells.

An antibody that is employed in the invention can be in any format. For example, in some embodiments, the antibody can be a complete antibody including a constant region, e.g., a human constant region, or can be a fragment or derivative of a complete antibody, e.g., a Fab, Fab', $F(ab')_2$, scFv, Fv, or a single domain antibody, such as a nanobody or a camelid antibody.

II. Heavy Chains

A heavy chain of an anti-PcrV antibody of the invention comprises a heavy-chain V-region that comprises the following elements:

1) human heavy-chain V-segment sequences comprising FR1-CDR1-FR2-CDR2-FR3

2) a CDRH3 region comprising the amino acid sequence NRGDIYYDFTY (SEQ ID NO:33)

3) a FR4 contributed by a human germ-line J-gene segment. Examples of V-segment sequences that support binding to PcrV in combination with a CDR3-FR4 segment described above together with a complementary $V_L$ region are shown in FIG. 1. The V-segments can be from the human VH1 or VH3 sub-classes. In some embodiments, the V-segment is a human $V_H3$ sub-class segment that has a high degree of amino-acid sequence identity with the germ-line segment VH3-30.3. For example the V-segment differs by not more than fifteen residues from VH3-30.3 and preferably not more than seven residues.

The FR4 sequence of the antibodies of the invention is provided by a human J segment. There are six heavy chain JH-regions numbered 1 through 6. Thus, the FR4 sequences can be provided by a JH1, JH2, JH3, JH4, JH5 or JH6 gene segment. Typically, the FR4 region of an antibody of the invention has at least 90%, often at least 91%, 92%, 93%, 94%, 95% 96%, 97%, 98%, 99%, or 100% identity, to the FR4 region of the human germline J segment that provides the FR4.

In some embodiments, the FR4 sequence is provided by a human germ-line JH3 segment and has a sequence WGQGTMVTVSS (SEQ ID NO:94). In other embodiments, the FR4 is provided by a human germ-line JH6 segment and has the sequence WGQGTTVTVSS (SEQ ID NO:95).

The CDRH3 also comprises sequences that are derived from a human J-segment. Typically, the CDRH3-FR4 sequence excluding the BSD differs by not more than 2 amino acids from a human germ-line J-segment. In typical embodiments, the J-segment sequences in CDRH3 are from the same J-segment used for the FR4 sequences. Thus, in some embodiments, the CDRH3-FR4 region comprises the BSD and a complete human JH3 germ-line gene segment. Exemplary combinations of CDRH3 and FR4 sequences are shown below, in which the BSD is in bold and human germ-line J-segment residues are underlined:

CDR3 (SEQ ID NO: 96)
NRGDIYYDFTYAFDIWGQGTMVTVSS (FR4 = JH3)

(SEQ ID NO: 97)
NRGDIYYDFTYAMDIWGQGTMVTVSS (FR4 = JH3)

(SEQ ID NO: 98)
NRGDIYYDFTYAMDIWGQGTTVTVSS (FR4 = JH6)

In some embodiments, an antibody of the invention comprises a V-segment that has at least 90% identity, or at least 91%, 92% 93%, 94%, 95%, 96%, 97%, 98%, 99%, or 100% identity to the germ-line segment VH3 30.3 or to a germline VH1-18 segment; or to one of the V-segments of the $V_H$ regions shown in FIG. 1, such as a V-segment portion of SEQ ID NOS:1, 3, 5, 7, 9, 11, 13, 15, 17, 19, 21, 23, 25, 26, 27, 29, and 35.

In some embodiments, the V-segment of the VH region has a CDR1 and/or CDR2 as shown in FIG. 1. For example, an antibody of the invention may have a CDR1 that has the sequence TAGMH (SEQ ID NO:50), SYGIH (SEQ ID NO:51), SYGMH (SEQ ID NO:52), SYPLH (SEQ ID NO:53), or NYPMH (SEQ ID NO:54); or a CDR2 that has the sequence VIWYNGKEISYADSVKG (SEQ ID NO:55), FISYDGSEKYYASSVKG (SEQ ID NO:56), or VISYDGSEKWYADSVKG (SEQ ID NO:57). In some embodiments, the CDR2 of the VH region has a negatively charged amino acid positioned in about the middle, e.g., at position 8 or 9 of the CDR2.

In particular embodiments, an antibody has both a CDR1 and a CDR2 from one of the $V_H$ region V-segments shown in FIG. 1 and a CDR3 that comprises NRGDIYYDFTY (SEQ ID NO:38), e.g., NRGDIYYDFTYAFDI (SEQ ID NO:63) or NRGDIYYDFTYAMDI (SEQ ID NO:99). Thus, an anti-PcrV antibody of the invention, may for example, have a CDR3-FR4 that has the sequence NRGDIYYDFTYAFDI- WGQGTMVTVSS (SEQ ID NO:96), NRGDIYYDFTYAMDIWGQGTMVTVSS (SEQ ID NO:97), or NRGDIYYDFTYAMDIWGQGTTVTVSS (SEQ ID NO:98). In other embodiments, the antibody may comprise a CDR3 that has the sequence NRGDIYYDFTYA(M/F)D(Q/S) (SEQ ID NO:100).

III. Light Chains

A light chain of an anti-PcrV antibody of the invention comprises at light-chain V-region that comprises the following elements:

1) human light-chain V-segment sequences comprising FR1-CDR1-FR2-CDR2-FR3

2) a CDRL3 region comprising the sequence FWXTP (where X may be S or G; SEQ ID NO:39)

3) a FR4 contributed by a human germ-line J-gene segment. The $V_L$ region comprises either a Vlambda or a Vkappa V-segment. Examples of Vlambda and Vkappa sequences that support binding in combination with a complementary $V_H$-region are provided in FIG. 2. Vkappa segments are cloned upstream of the human germ-line JK2 segment and Vlambda segments are cloned upstream of the germ-line JL2 segment.

The CDRL3 sequence comprises a V-segment and J-segment derived sequences. In typical embodiments, the J-segment sequences in CDRL3 are from the same J-segment used for FR4. Thus, may differ by not more than 2 amino acids from human kappa germ-line V-segment and J-segment sequences. In some embodiments, the CDRL3-FR4 region comprises the BSD and the complete human JK2 germ-line gene segment. Exemplary CDRL3-FR4 combinations for kappa chains are shown below in which the BSD is shown in bold and JK2 sequences are underlined:

```
CDR3                          (SEQ ID NO: 101)
QQFWSTPYTFGQGTKLEIK (JK2)

                              (SEQ ID NO: 102)
QHFWGTPYTFGQGTKLEIK (JK2)
```

A preferred CDR3-FR4 for lambda chains is shown below in which the BSD is shown in bold and the JL2 sequences are underlined:

```
CDR3                          (SEQ ID NO: 103)
QHFWSTPYTFGGGTKLTVL (JL2)
```

The FR4 sequence of the antibodies of the invention is provided by a human J segment. There are five human JKappa-region segments labeled 1 though 5 and four JLambda-region segments labeled 1, 2, 3 and 7. Thus, the FR4 sequences can be provided by any of these germline sequences. Typically, the FR4 region of an antibody of the invention has at least 90%, often at least 91%, 92%, 93%, 94%, 95% 96%, 97%, 98%, 99%, or 100% identity, to the FR4 region of the human germline J segment that provides the FR4.

The Vkappa segments are typically of the VKI or VKIII sub-class. In some embodiments, the segments have at least 80% sequence identity to a human germline VKI or VKIII subclass, e.g., at least 80% identity to the human germ-line VKI L12 sequence or to human germline VKIII L2 or VKIIIA11 sequence. For example, the Vkappa segment may differ by not more than 18 residues from VKI L12, or 12 residues from VKIII A11 or VKIII L2. In other embodiments, the $V_L$ region V-segment of an antibody of the invention has at least 85% identity, or at least 90%, 91%, 92%, 93%, 94%, 95%, 96%, 97%, 98%, 99%, or 100% identity to the human germline VKI L12, or to the human germline VkIII L2 sequence, or to human germline VKIII A11 sequence, or to a kappa V-segment sequence of a $V_L$ region shown in FIG. 2, for example, the V-segment sequence of SEQ ID NOS:2, 4, 6, 8, 10, 12, 14, 16, 18, 20, 22, 24, or 37.

In some embodiments, the V-segment of the $V_L$ corresponds to a human germline Vlambda segment. Thus, in some embodiments, the V-segment has at least 85% identity, or at least 90%, 91%, 92%, 93%, 94%, 95%, 96%, 97%, 98%, 99%, or 100% identity to a Vlambda V-segment of a $V_L$ region of FIG. 2, such as the V-segment sequence of SEQ ID NOS: 28, 30, 32, or 34.

In some embodiments, the V-segment of the $V_L$ region has a CDR1 and/or CDR2 as shown in FIG. 2. For example, an antibody of the invention may have a CDR1 sequence of RASQGISTYLA (SEQ ID NO:66), RASQGISSWLA (SEQ ID NO:67), RASQSISRWVA (SEQ ID NO:68), or RASEGVDRWLA (SEQ ID NO:69) or CDR2 sequence AASSLQS (SEQ ID NO:70), DASSLKS (SEQ ID NO:71), DASALQS (SEQ ID NO:72), or DASTLQS (SEQ ID NO:73). In other embodiments, the antibody may have a CDR1 sequence of QGDSLRSYYA (SEQ ID NO:104), TGTSSDVGAYNYVS (SEQ ID NO:79), or TGTSSDYV (SEQ ID NO:105); or a CDR2 sequence GKNNRPS (SEQ ID NO:106), EVTKRPS (SEQ ID NO:107), or DVTNRPS (SEQ ID NO:108).

In particular embodiments, an anti-PcrV antibody of the invention may have a CDR1 and a CDR2 in a combination as shown in one of the V-segments of the $V_L$ regions set forth in FIG. 2 and a CDR3 sequence that comprises FWXTP (SEQ ID NO:39), where X is S or G, e.g., the CDR3 may be QQFWSTPYT (SEQ ID NO:109), QHFWGTPYT (SEQ ID NO:110), or QHFWSTPYT (SEQ ID NO:111). In some embodiments, such an anti-PcrV antibody may comprise an FR4 region that is FGQGTKLEIK (SEQ ID NO:47) or FGGGTKLTVL (SEQ ID NO:48). Thus, an anti-PcrV antibody of the invention, can comprise, e.g., both the CDR1 and CDR2 from one of the $V_L$ regions shown in FIG. 2 and a CDR3-FR4 region that is QQFWSTPYTFGQGTKLEIK (SEQ ID NO:101), QHFWGTPYTFGQGTKLEIK (SEQ ID NO:102), or QHFWSTPYTFGGGTKLTVL (SEQ ID NO:103).

IV. Preparation of PcrV Antibodies

An antibody of the invention may comprise any of the $V_H$ regions of SEQ ID NOS:1, 3, 5, 7, 9, 11, 13, 15, 17, 19, 21, 23, 25, 26, 27, 29, or 35 in combination with any of the $V_L$ regions of SEQ ID NOS:2, 4, 6, 8, 10, 12, 14, 16, 18, 20, 22, 24, 28, 30, 32, 34, 36 or 37.

An antibody may be tested to confirm that the antibody retains the activity of antagonizing the Type III secretion system. The antagonist activity can be determined using any number of endpoints, including cytotoxicity assays. Exemplary assays are described, e.g., in U.S. Pat. No. 6,827,935. An antibody that is administered to treat *P. aeruginosa* infection preferably retains at least 75%, preferably 80%, 90%, 95%, or 100%, of the Type III secretion pathway antagonist activity of Mab 166 (U.S. Pat. No. 6,827,935).

A high-affinity antibody may be identified using well known assays to determine binding activity and affinity. Such techniques include ELISA assays as well as binding determinations that employ surface plasmon resonance or interferometry. For example, affinities can be determined by biolayer interferometry using a ForteBio (Mountain View, Calif.) Octet biosensor.

Antibodies of the invention typically compete with Mab166 for binding to PcrV. The region of PcrV to which Mab166 binds has been identified (U.S. Pat. No. 6,827,935). PcrV or a fragment thereof that binds Mab166 can be employed in a competitive binding assay. The ability of an antibody described herein to block or compete with Mab166 for binding to PcrV indicates that the antibody binds to the same epitope as Mab166 or to an epitope that is close to, e.g., overlapping, with the epitope that is bound by Mab166. In other embodiments an antibody described herein, e.g., an antibody comprising a $V_H$ and $V_L$ region combination as shown in Table 1, can be used as a reference antibody for assessing whether another antibody competes for binding to PcrV. A test antibody is considered to competitively inhibit binding of a reference antibody, if binding of the reference antibody to the antigen is reduced by at least 30%, usually at least about 40%, 50%, 60% or 75%, and often by at least about 90%, in the presence of the test antibody. Many assays can be employed to assess binding, including ELISA, as well as other assays, such as immunoblots.

In some embodiments, the anti-PcrV antibody need not antagonize the Type III secretion sequences. For example, antibodies of the invention that bind to PcrV can recruit multiple cell types of the immune system to stimulate phagocytosis by macrophages, antibody directed cellular cytotoxicity (ADCC) by macrophages or NK cells, activation of the complement cascade, and/or generation of the oxidative burst by neutrophils, thereby causing bacterial, i.e., *P. aeruginosa*, death. Furthermore, all antibody variable regions are capable of catalyzing redox reactions from singlet oxygen provided by activated neutrophils, leading to the generation of a variety of highly potent oxidizing agents directly harmful to bacteria (see, e.g., Wentworth et al., *Proc. Natl. Acad. Sci. USA* 97:10930-10935, 2000), including ozone, a potent antibacterial agent which also stimulates inflammatory responses (see, e.g., Babior et al., *Proc. Natl. Acad. Sci. USA* 100:3031-3034, 2003). Indeed, inflammation induced by complement activation and ozone generation has the potential to recruit additional elements of the immune system to further boost immunity. Such antibodies typically have an affinity of 50 nM or less, typically less than about 10 nM.

Non-neutralizing and neutralizing anti-PcrV antibodies used in combination with antibiotics provide a strong therapeutic effect.

Methods for the isolation of antibodies with V-region sequences close to human germ-line sequences have previously been described (US patent applications 20050255552 and 20060134098). Antibody libraries may be expressed in a suitable host cell including mammalian cells, yeast cells or prokaryotic cells. For expression in some cell systems, a signal peptide can be introduced at the N-terminus to direct secretion to the extracellular medium. Antibodies may be secreted from bacterial cells such as *E. coli* with or without a signal peptide. Methods for signal-less secretion of antibody fragments from *E. coli* are described in US patent application 20070020685.

To generate a PcrV-binding antibody, one of the $V_H$-regions of the invention is combined with one of the $V_L$-regions of the invention and expressed in any of a number of formats in a suitable expression system. Thus the antibody may be expressed as a scFv, Fab, Fab' (containing an immunoglobulin hinge sequence), F(ab')$_2$, (formed by di-sulfide bond formation between the hinge sequences of two Fab' molecules), whole immunoglobulin or truncated immunoglobulin or as a fusion protein in a prokaryotic or eukaryotic host cell, either inside the host cell or by secretion. A methionine residue may optionally be present at the N-terminus, for example, in polypeptides produced in signal-less expression systems. Each of the $V_H$-regions described herein may be paired with each of the $V_L$ regions to generate an anti-PcrV antibody. For example, VH3 1080-2F was identified from the library paired with two different lambda light chains (1080-2F and 1080-11E). The kappa chain 1069-3F was identified paired with VH3 1069-3F and with VH3 1100-3. Exemplary combinations of heavy and light chains are shown in the Table 1.

TABLE 1

Exemplary antibody heavy-chain and light-chain combinations

| VH | |
|---|---|
| | Vkappa |
| SEQ ID NO: 1 | SEQ ID NO: 2 |
| SEQ ID NO: 11 | SEQ ID NO: 12 |
| SEQ ID NO: 3 | SEQ ID NO: 12 |
| SEQ ID NO: 7 | SEQ ID NO: 8 |
| SEQ ID NO: 9 | SEQ ID NO: 10 |
| SEQ ID NO: 5 | SEQ ID NO: 6 |
| SEQ ID NO: 13 | SEQ ID NO: 37 |
| SEQ ID NO: 21 | SEQ ID NO: 18 |
| SEQ ID NO: 17 | SEQ ID NO: 18 |
| SEQ ID NO: 26 | SEQ ID NO: 24 |
| SEQ ID NO: 25 | SEQ ID NO: 24 |
| SEQ ID NO: 23 | SEQ ID NO: 24 |
| SEQ ID NO: 29 | SEQ ID NO: 20 |
| SEQ ID NO: 35 | SEQ ID NO: 36 |
| | Vlambda |
| SEQ ID NO: 29 | SEQ ID NO: 28 |
| SEQ ID NO: 29 | SEQ ID NO: 30 |
| SEQ ID NO: 29 | SEQ ID NO: 34 |
| SEQ ID NO: 3 | SEQ ID NO: 32 |

In many embodiments, the antibodies of the invention antagonize the *P. aeruginosa* type III secretion system and typically exhibit high affinity binding to PcrV. High affinity binding between an antibody and an antigen exists if the affinity of the antibody is less than 500 or 100 nM, for example, less than 50 nM or less than 25 nM, or less than 10 nM, or less than 1 nM, e.g., less than about 100 pM. The antibodies of the invention typically have an affinity of 50 mM or less, often 10 nM or less, when assayed as Fabs, e.g., using ELISA, surface plasmon resonance assays, or interferometry. Table 1 provides examples of such antibodies.

In some embodiments, an antibody of the invention is more potent in a cellular cyototxicity assay than Mab166.

Antibodies may be produced using any number of expression systems, including both prokaryotic and eukaryotic expression systems. Many such systems are widely available from commercial suppliers. In embodiments in which an antibody comprises both a $V_H$ and $V_L$ region, the $V_H$ and $V_L$ regions may be expressed using a single vector, e.g., in a discistronic expression unit, or under the control of different promoters. In other embodiments, the $V_H$ and $V_L$ region may be expressed using separate vectors. The antibodies of the invention may be expressed with or without a methionine at the N-terminus. Thus, a $V_H$ or $V_L$ region as described herein may optionally comprise a methionine at the N-terminus.

An antibody of the invention may be produced in any number of formats, including as a Fab, a Fab', a F(ab')$_2$, a scFv, or a dAB. An antibody of the invention can also include a human constant region. The constant region of the light chain may be a human kappa or lambda constant region. The heavy chain constant region is often a gamma chain constant region, for example, a gamma-1, gamma-2, gamma-3, or gamma-4 constant region. In other embodiments, the antibody may be an IgA.

In some embodiments, the antibody is "non-immunogenic" when administered to a human. The term "non-immunogenic" as used here refers to a PcrV antibody of the invention that does not provoke antibody production against the anti-PcrV antibody when administered to a human. Antibodies can be assessed for immunogenicity using known assays, e.g., an electrochemiluminescence immunoassay described in example 5. Such assays detect the level of antibodies present in a patient, e.g., in a serum sample from the patient, that react with the anti-PcrV antibody that is administered to the patient. An assay is considered to show that the antibody is non-immunogenic when no detectable antibody to the anti-PcrV antibody is present in the sample, e.g., in comparison to a control sample from an individual that was not administered the antibody.

V. PEGylation of Antibodies

In some embodiments, e.g., where the antibody is a fragment, the antibody can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20: 227, 2007).

In some embodiments, the antibodies of the invention are in the form of a Fab' fragment. A full-length light chain is generated by fusion of a $V_L$-region to human kappa or lambda constant region. Either constant region may be used for any light chain; however, in typical embodiments, a kappa constant region is used in combination with a Vkappa variable region and a lambda constant region is used with a Vlambda variable region.

The heavy chain of the Fab' is a Fd' fragment generated by fusion of a $V_H$-region of the invention to human heavy chain constant region sequences, the first constant (CH1) domain and hinge region. The heavy chain constant region sequences can be from any of the immunoglobulin classes, but is often from an IgG, and may be from an IgG1, IgG2, IgG3 or IgG4. The Fab' antibodies of the invention may also be hybrid sequences, e.g., a hinge sequence may be from one immunoglobulin sub-class and the CH1 domain may be from a different sub-class. In a preferred embodiment, the heavy chain constant region including the CH1 domain and hinge sequence is from human IgG1.

The Fab' molecule can be PEGylated using known methods. The hinge region of the heavy chain contains cysteine residues suitable for conjugation to a polyethylene glycol derivative. The hinge sequence may be the complete natural hinge region of an immunoglobulin heavy chain or may be truncated by one or more amino-acids. In some embodiments, the hinge region may be a modified or synthetic sequence. In further embodiments, the hinge is a natural immunoglobulin hinge sequence and contains two cysteine residues.

In some embodiments, Fab' molecules can be conjugated by site-specific conjugation to maleimide derivatives of methoxy polyethylene glycol (mPEG-mal). The mPEG-mal can have, for example, an average molecular mass of between 10 and 40 kD. The PEG may be branched PEG or linear PEG. In some embodiments, the mPEG-mal is a linear molecule and has an approximate molecular weight of 30 kD. One or more molecules of mPEG-mal is conjugated to each Fab' molecule. The mPEG molecules are conjugated via thioether linkages between the maleimide moiety of mPEG-mal and one or more of the cysteine residues in the hinge region of the Fab' heavy chain to form the PEGylated Fab' molecule. The mPEG-mal is conjugated in suitable buffer and under conditions suitable for thioether formation using methods known in the art for conjugation of maleimide derivatives to thiol-groups on proteins.

The Fab' may be produced from the expression system in a form in which the hinge cysteine groups are in an oxidized form. In this case, the Fab' may be subjected to a reduction step prior to conjugation. Reducing agents suitable for generation of free hinge thiols and methods for selective reduction of hinge cysteines are known in the art and include the use of dithiothreitol (DTT), beta-mercapto-ethanol, beta-mercapto-ethylamine (MEA) and non-thiol reducing agents such as tris(2-carboxyethyl) phosphine. In some embodiments, the reduction is carried out under conditions such that the hinge cysteines are selectively reduced and PEGylation occurs predominantly at the hinge. Typically, the PEGylated Fab' comprises two molecules of mPEG due to PEGylation of both cysteine residues in the hinge. In some embodiments, a mutation may be introduced into the hinge region to replace one of the cysteine residues with another amino acid. Derivatization of such a mutant with mPEG-mal leads to the generation of mono-PEGylated Fab'.

Examples of suitable sequences of hinges are:

```
natural human gamma-1 hinge for di-PEGylation
THTCPPCPA                          (SEQ ID NO: 112)

Mutant Hinge-1 for mono-PEGylation
THTAPPCPA                          (SEQ ID NO: 113)

Mutant Hinge-2 for mono-PEGylation
THTCPPAPA
```

Other methods of PEGylation, for example, where the PEG is not introduced at a hinge are also known. For example, Humphreys et al., supra, describe methods for PEGylation of cysteine residues outside the hinge region by disruption of the interchain disulphide bond between the heavy and light chain of a Fab.

Methods for purification of PEGylated Fab' and separation of the desired mono- or di-PEGylated Fab' from unreacted mPEG-maleimide and Fab' molecules containing higher numbers of PEG moieties are known in the art. Such methods include, for example, size-exclusion or ion-exchange chromatography.

VI. Administration of PcrV Antibodies for the Treatment of *P. Aeruginosa* Infections.

The invention also provides methods of treating a patient that has, or is at risk of having, a *P. aeruginosa* infection by administering an antibody of the invention. In some embodiments, such a patient has cystic fibrosis, ventilator-associated pneumonia (VAP), cancer-associated neutropenia, or burns. The methods of the invention comprise administering a PcrV antibody as a pharmaceutical composition to an *P. aeruginosa*-infected patient in a therapeutically effective amount using a dosing regimen suitable for treatment of the disease. The composition can be formulated for use in a variety of drug delivery systems. One or more physiologically acceptable excipients or carriers can also be included in the compositions for proper formulation. Suitable formulations for use in the present invention are found in *Remington's Pharmaceutical Sciences*, Mack Publishing Company, Philadelphia, Pa., 17th ed. (1985). For a brief review of methods for drug delivery, see, Langer, Science 249: 1527-1533 (1990).

The PcrV antibody is provided in a solution suitable for injection into the patient such as a sterile isotonic aqueous solution for injection. The antibody is dissolved or suspended at a suitable concentration in an acceptable carrier. In some embodiments the carrier is aqueous, e.g., water, saline, phosphate buffered saline, and the like. The compositions may contain auxiliary pharmaceutical substances as required to approximate physiological conditions, such as pH adjusting and buffering agents, tonicity adjusting agents, and the like.

The pharmaceutical compositions of the invention are administered to a patient, e.g., a cystic fibrosis patient having a *P. aeruginosa* infection, in an amount sufficient to cure or at least partially arrest the disease or symptoms of the disease and its complications. An amount adequate to accomplish this is defined as a "therapeutically effective dose." A therapeutically effective dose is determined by monitoring a patient's response to therapy. Typical benchmarks indicative of a therapeutically effective dose include amelioration of symptoms of infection in the patient, or a decrease in the levels of *P. aeruginosa* in the patient. Amounts effective for this use will depend upon the severity of the disease and the general state of the patient's health, including other factors such as age, weight, gender, administration route, etc. Single or multiple administrations of the antibody may be administered depending on the dosage and frequency as required and tolerated by the patient. In any event, the methods provide a sufficient quantity of PcrV antibody to effectively treat the patient.

The antibody may be administered alone, or in combination with other therapies to treat the *P. aeruginosa* infection The antibody can be administered by injection or infusion through any suitable route including but not limited to intravenous, sub-cutaneous, intramuscular or intraperitoneal routes. In some embodiments, the antibody may be administered by insufflation. In an exemplary embodiment, the antibody may be stored at 10 mg/ml in sterile isotonic aqueous saline solution for injection at 4° C. and is diluted in either 100 ml or 200 ml 0.9% sodium chloride for injection prior to administration to the patient. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via sub-cutaneous bolus injection.

The dose of antibody is chosen in order to provide effective therapy for the patient and is in the range of less than 0.1 mg/kg body weight to 25 mg/kg body weight or in the range 1 mg-2 g per patient. Preferably the dose is in the range 1-10 mg/kg or approximately 50 mg-1000 mg/patient. The dose may be repeated at an appropriate frequency which may be in the range once per day to once every three months, depending on the pharmacokinetics of the antibody (e.g. half-life of the antibody in the circulation) and the pharmacodynamic response (e.g. the duration of the therapeutic effect of the antibody). In some embodiments, the in vivo half-life of between about 7 and about 25 days and antibody dosing is repeated between once per week and once every 3 months. In other embodiments, the antibody is administered approximately once per month.

In further embodiments, the antibody is PEGylated. For example, an antibody of the invention may be PEGylated, e.g., using methods as described herein, and administered to a patient infected with *P. aeruginosa*.

A $V_H$ region and/or $V_L$ region of the invention may also be used for diagnostic purposes. For example, the $V_H$ or $V_L$ region may be used for clinical analysis, such as detection of *P. aeruginosa* in samples from patient that have, or are suspected of having, a *P. aeruginosa* infection. A $V_H$ or $V_L$ region of the invention may also be used, e.g., to produce anti-Id antibodies.

EXAMPLES

Example 1

Identification of Engineered Human Anti-PcrV Fab Molecules

Epitope-focused engineered human antibody Fab libraries were generated as described in US patent application 20050255552. V-segment sequences derived from repertoires of human immunoglobulin sequences were cloned upstream of a selected CDR3-FR4 sequence for each of the heavy and light chains.

For heavy-chain repertoires, the CDRH3 comprises a D-segment derived sequence (NRGDIYYDFTY; SEQ ID NO:38) from a previously identified anti-PcrV monoclonal antibody (Mab 166; Frank et al 2002 J. Infectious Dis. 186: 64-73) which constitutes a binding specificity determinant. The sequence of the complete CDRH3-FR4 sequence for the heavy chain repertoires is shown below.

For VH1 library 1015, the CDR3-FR4 combination used was:

```
    CDR3                             (SEQ ID NO: 96)
NRGDIYYDFTYAFDIWGQGTMVTVSS (FR4 = JH3)
```

For VH3 libraries, the CDR3-FR4 combination used differed by a single amino acid in CDRH3:

```
    CDR3                             (SEQ ID NO: 97)
NRGDIYYDFTYAMDIWGQGTMVTVSS (FR4 = JH3)
```

For light-chain repertoires, human Vkappa or Vlambda sequences comprising FR1-CDRL1-FR2-CDRL2-FR3 were inserted upstream of selected CDRL3-FR4 sequences. The CDRL3 comprises a binding specificity determinant from Mab 166 light-chain with the sequence FWXTP (where X may be S or G; SEQ ID NO:39). For Vkappa libraries, the C-terminal residues of CDRL3 and FR4 were contributed by the human germ-line JK2 sequence YTFGQGTKLEIK (SEQ ID NO:115) (JK2 residues within CDRL3 are underlined). For Vlambda libraries, the FR4 region was contributed by JL2 germ-line sequence FGGGTKLTVL (SEQ ID NO:48). The JL2 germline sequence is identical to the JL3 sequence.

In some cases cassette libraries were constructed as described in US patent application 20060134098 (library 1070). For library 1080, full-length lambda chains were screened in combination with VH cassette libraries.

Heavy and light chain polypeptides were expressed as mature proteins, i.e., without a signal peptide, and secreted in *E. coli* cells that express a mutant SecY gene as described in US patent application 20070020685. The peptides therefore were expressed with an N-terminal methionine. Binding of recombinant Fabs to PcrV was identified by a filter-binding assay using nitrocellulose filters coated with GST-PcrV fusion protein as described in US patent application 20050255552. Binding activity was confirmed by antigen ELISA using plates coated with GST-PcrV and affinities were determined by biolayer interferometry using a ForteBio Octet biosensor.

The sequences of the V-regions of exemplary high-affinity anti-PcrV antibodies are shown in FIG. 1 and FIG. 2.

Each of the Fabs has high affinity for PcrV. Several Fabs were identified with affinities at least equivalent to Mab166 Fab (approximately 1.4 nM) determined by biolayer interferometry using a ForteBio (Mountain View, Calif.) Octet biosensor.

VH and VL regions identified as described can be used in various combinations. For example, a $V_K$ light chain SEQ ID NO: 12 supports high affinity binding to PcrV in combination with either a $V_H$ comprising SEQ ID NO: 11, or a $V_H$ comprising SEQ ID NO:3.

The 1070-9E antibody is an example of a high affinity antibody derived by V-region cassette exchange using methods described in US Patent Application Publication No.

20060134098. To isolate this antibody, 4 V-region replacement cassettes were constructed:

1) heavy chain front-end cassette (consisting of human VH3 FR1-CDR1-FR2 sequences)

2) heavy chain middle cassette (consisting of human VH3 FR2-CDR2-FR3 sequences)

1) light chain front-end cassette (consisting of human VK1 FR1-CDR1-FR2 sequences)

2) light chain middle cassette (consisting of human VK1 FR2-CDR2-FR3 sequences).

Each cassette was assembled with additional V-region sequences from Mab 166 and the selected CDR3-FR4 region and expressed as Fab fragments in *E. coli* TOP10 cells transformed with a plasmid over-expressing a mutant SecY gene to allow secretion of signal-less Fabs. Cassette Fab libraries were then screened on GST-PcrV coated filters to identify PcrV binders. Selected sequences from Fabs supporting PcrV binding were then recombined and re-screened to identify fully-human V-segments supporting high-affinity binding to PcrV.

Fab 1070-9E, isolated by cassette recombination, has an affinity for recombinant PcrV of 1.48 nM, determined by biolayer interferometry.

High-affinity anti-PcrV Fabs are also potent antagonists of the *P. aeruginosa* Type III Secretion system and inhibit *P. aeruginosa* exotoxin-mediated killing of P3-X63 Ag8 myeloma cells by *P. aeruginosa* strain PA103 in a cell-based cytotoxicity assay.

Example 2

PEGylated Fab'

In this example, a Fab' consisting of a human Fd' heavy chain of the IgG1 sub-class and human kappa light chain linked by an inter-chain disulfide bond involving the C-terminal cysteine of the kappa chain and the cysteine residue C227 of the heavy chain (numbering sequentially from the N-terminus of the mature protein) was PEGylated. The recombinant Fd' heavy chain contains the IgG1 CH1 domain and the IgG1 hinge region including two cysteine residues which are available after reduction for conjugation to maleimide groups. Thus the expressed antibody protein is a disulfide-linked heterodimer of Fd' heavy chain and a kappa light chain, containing a total of 452 amino acids. The sequence of the constant region of an exemplary Fd' is shown in FIG. 3.

To generate an immunoconjugate with a reduced rate of in vivo clearance and thus an improved pharmacokinetic profile, the Fab' is conjugated to polyethylene glycol (PEG). In di-PEGylated Fab', each molecule of Fab' is conjugated to two long-chain PEG molecules by site-specific attachment at the hinge region exploiting the two available reactive thiols on the hinge cysteine residues and a maleimide derivatized PEG, methoxy-polyethylene glycol maleimide (mPEG-mal). The mPEG-mal molecules are conjugated via thioether linkages between the maleimide moiety and the hinge cysteine residues.

To generate di-PEGylated Fab', mPEG-mal with average molecular weight of 30 kD was obtained from NOF Corporation. The Fab', which was expressed and secreted from *E. coli*, was prepared at a concentration of 4 mg/ml in sodium citrate buffer pH 6.5 with 2 mM EDTA. Reducing agent (10 mM MEA at pH 6.5) was added for 30 minutes at room temperature and the reaction mixture was immediately desalted using a Zeba Desalt column (Pierce) pre-equilibrated with 10 mM glycine (pH 3) and 2 mM EDTA. mPEG-mal was added for 1 hour at room temperature and di-PEGylated Fab' was separated from other PEGylated species and from unreacted Fab' using a HiTrap SP sepharose column on an Akta purification system from GE Healthcare.

The structure of di-PEGylated Fab' is provided schematically in FIG. 4. The exemplary di-PEGylated Fab' PEGylated in this example binds with high affinity to PcrV (affinity of 0.6 nM determined by surface plasmon resonance analysis) and is a potent antagonist of the *P. aeruginosa* Type III Secretion System.

Mono-PEGylated Fab' can be generated using mutant derivatives of Fab' containing only a single hinge cysteine. The sequences of the mutant hinges are:

```
Wild-type human gamma-1 hinge
THTCPPCPA                    (SEQ ID NO: 112)

Mutant Hinge-1
THTAPPCPA                    (SEQ ID NO: 113)

Mutant Hinge-2
THTCPPAPA                    (SEQ ID NO: 114)
```

Example 3

Cytotoxicity Assay for Detection of Antibodies and Fab Fragments with Potent Neutralization Activity Against the *P. aeruginosa* Type III Secretion System A TTSS-dependent cytotoxicity assay was established using P3-X63-Ag8 (X63) mouse myeloma cells (ATCC) as the target. Cells were cultured in RPMI 1640 (Media Tech) with 10% FBS (Hyclone). About $10^5$ cells were infected with *P. aeruginosa* strain PA103 at a multiplicity of infection (MOI) of 10 in a volume of 0.1 ml culture medium in wells of a 96-well plate in the presence of Fab. Prior to addition of Fab and mammalian cells, PA103 was grown in MinS medium (Hauser A R et al. (1998) *Infect Immun.* 66:1413-1420) to induce expression of the TTSS. After incubation for three hours at 37° C. with 5% CO2, with various concentrations of anti-PcrV Fab, cells were transferred to 12×75 mm flow-cytometry tubes and stained with propidium iodide (Sigma) according to the manufacturer's instructions. The proportion of permeabilized cells was quantified by flow cytometry using a FACS Caliber flow cytometer. Data were analyzed using Prism4 software (Graphpad). (Cytotoxicity was normalized to dead cells in untreated samples). For comparison of the potency of different Fabs, mean concentrations required for 50% inhibition ($IC_{50}$) were obtained from at least 3 independent assays. Results for several exemplary Fabs are shown in Table 2 below.

TABLE 2

Potency of Fabs in cytotoxicity assay

| Fab | $IC_{50}$ (nM) |
|---|---|
| Mab166 Fab | 53.0 |
| SEQ ID NOS: 13, 4 | 20.0 |
| SEQ ID NOS: 13, 37 | 12.0 |
| SEQ ID NOS: 5, 6 | 50.2 |
| SEQ ID NOS: 13, 10 | 25.5 |
| SEQ ID NOS: 3, 4 | 35.1 |
| SEQ ID NOS: 24, 26 | 25.5 |
| SEQ ID NOS: 35. 36 | 61.4 |

Each of the Fabs tested shows potent neutralization of the TTSS and protection of mammalian cells from cytotoxicity.

Several Fabs are more potent in this assay than Mab 166 Fab. Thus, anti-PcrV antibodies of the invention typically show enhanced potency relative to Mab 166 Fab.

Example 4

Effects of an Antibody of the Invention In Vivo Using a Mouse Model of Pneumonia Experiments were performed in vivo using humaneered Fabs to evaluate the effects of the antibodies in a mouse model of pneumonia. Fab 1A8 has a human VH3 sub-class heavy chain, containing the first constant domain of human IgG1, and a human VKI sub-class kappa light chain. The affinity of Fab 1A8 as determined by Biacore is 0.6 nM. Fab 1A8 binds to PcrV with approximately two-fold higher affinity than Mab 166 Fab.

An acute lethality model of *Pseudomonas* pneumonia was used to assess the in vivo efficacy of Fab 1A8 in comparison with Mab 166. *P. aeruginosa* strain PA103 was instilled directly into the lungs of mice at a dose of $1.5\times10^6$ cfu/mouse by intratracheal administration, an inoculum shown previously to be sufficient to lead to lethality in 100% of the animals ($3\times LD_{90}$) (Sawa et al., *Nat Med.* 5:392-8, 1999). Survival and body temperature were monitored for 48 hours and surviving mice at this time point were sacrificed for determination of bacterial counts in the lungs. The survival data (FIG. 5) indicated that both the human Fab 1A8 and the murine Fab can prevent lethality caused by the highly cytotoxic PA103 strain. Control mice infected with PA103 and treated with an irrelevant control Fab, were all dead within 24 hours of inoculation. Treatment of mice with 10 μg Mab 166 or Fab 1A8 led to the survival of 100% of the mice at 48 hours. Since Fab 1A8 lacks the antibody Fc-region, antibody effector functions are not required for prevention of lethality. Fab 1A8 was significantly more potent than Mab166 Fab in prevention of lethality. Fab 1A8 provided significant protection from lethality at doses of 1.25 μg and 0.625 μg/mouse, doses at which mouse Mab166 Fab-treated animals showed 100% mortality ($P<0.05$ for differences between Fab 1A8 and Mab 166 Fab at 2.5 μg, 1.25 μg and 0.625 μg doses). The activity of Fab 1A8 is comparable to that of Mab166 IgG in prevention of lethality.

Fab 1A8 is also effective in inducing recovery of body temperature, indicative of protection from sepsis (FIG. 6). Untreated mice infected with PA103 show a rapid drop in body temperature within the first few hours of infection. Recovery of body temperature within 12-24 hours in the antibody-treated groups correlates with subsequent survival. Doses as low as 1.25 μg/mouse of Fab 1A8 or Mab 166 led to rapid recovery of body temperature and prevented lethality in at least 80% of mice. However, this dose of mouse Mab 166 Fab fragment was insufficient to allow body temperature recovery and all mice in this group were dead at 48 hours post-infection.

Figure 7:
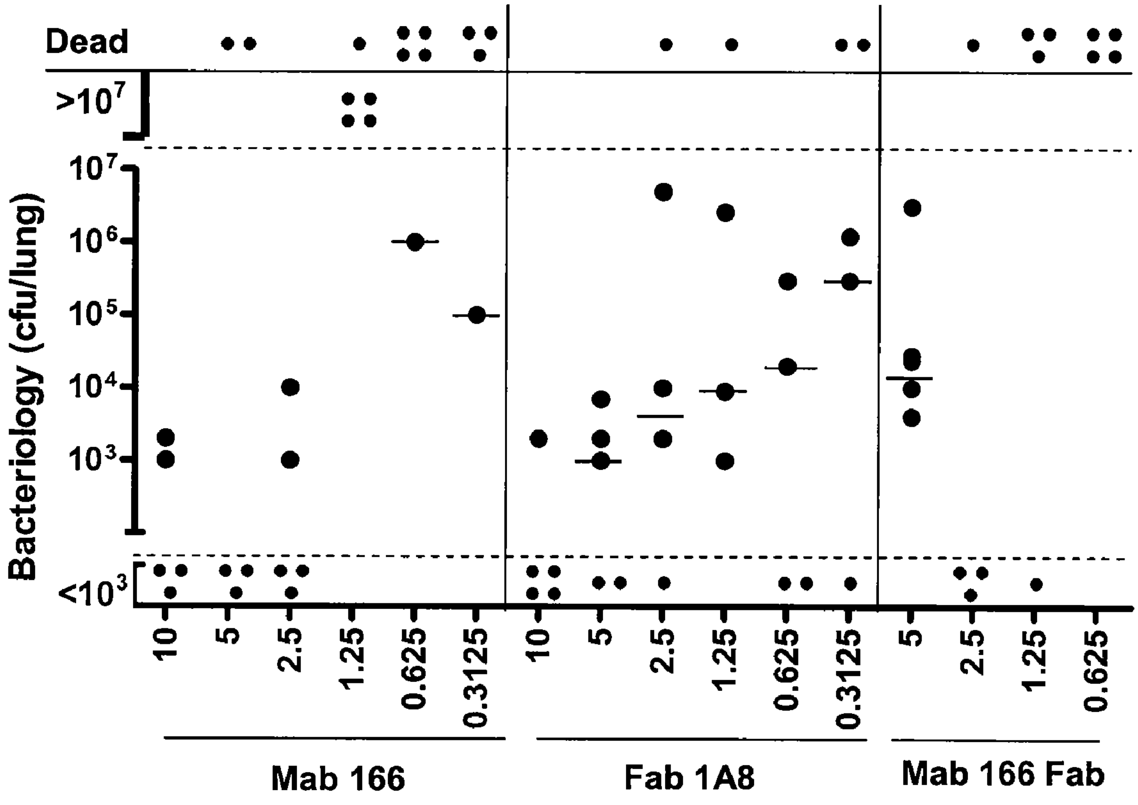
FIG. 7 provides data showing clearance of *P. aeruginosa* from the lungs of infected mice by anti-PcrV antibodies. Mice were infected with $1.5\times10^6$ cfu PA103 co-instilled with Mab 166 IgG, Mab 166 Fab or human Fab 1A8 at the doses shown (in μg). The graph shows cfu/lung isolated from individual mice surviving at 48 h. The number of dead mice at this time point is shown above the figure. Median cfu/lung for surviving mice in each group is shown with a bar.

Surviving mice at 48 hours post-challenge were also analyzed for the presence of residual *Pseudomonas* in the lungs. Remarkably, both Mab 166 and the Fab 1A8 fragments analyzed stimulated significant clearance of bacteria (FIG. 7). After 48 hours, the bacterial counts were reduced at least 1000-fold from the infectious dose of $1.5\times10^6$ cfu/mouse in all mice treated with 10 μg Fab 1A8. 80% of mice treated with this dose of Fab 1A8 showed no detectable *Pseudomonas* in the lungs after 48 hours. Higher residual bacterial counts were detected in mice treated with mouse Mab 166 Fab. Human Fab 1A8 has comparable potency to the whole IgG Mab 166 in this analysis indicating that Fc-effector functions do not contribute significantly to the ability of the antibody to stimulate bacterial clearance A second humaneered Fab that has the Mab 166 minimal essential binding specificity determinant was also evaluated in vivo using a mouse model of pneumonia. Female Balb/c mice (approximately 20 g in weight; Charles River) were inoculated with $1\times10^6$ *P. aeruginosa* strain PA103 by intratracheal administration. Prior to inoculation, PA103 bacteria were grown overnight in YPT broth at 37° C., diluted 1:5 in fresh medium and grown for two hours at 37° C. until they reached exponential phase. The culture was centrifuged at room temperature for ten minutes at 2000×g and the pellet resuspended in ~8 mL phosphate buffered saline (PBS). Bacteria were quantified by absorbance at 600 nm and bacterial colony-forming units verified by colony growth on tryptic soy (TS) agar plates (Teknova, Half Moon Bay, Calif.). Antibody Fab 2 fragment was premixed with bacteria immediately prior to intratracheal instillation. Infected mice were monitored for body temperature (rectal temperatures) and survival for 48 hours.

Control mice treated only with saline solution showed 100% mortality within 24 hours of bacterial inoculation. Mice treated with 10 μg Fab 2 showed complete protection from lethality; 100% of the Fab-treated mice survived at 48 hours.

This example thus shows that humaneered antibodies of the invention exhibit potent in vivo activity against *P. aeruginosa*. The Fabs are more potent than a parent M166 Fab in vivo.

Example 5

Evaluation of a Humaneered Fab for Immunogenicity in Human

A humaneered antibody PEGylated Fab' fragment was evaluated for safety, immunogenicity and plasma/serum half-life in human subjects. Subjects received one dose by intravenous (i.v.) injection at 1, 3, or 10 mg/kg.

The humaneered antibody was well tolerated at all dose levels. The concentration of drug in the plasma was measured by ELISA using the PcrV antigen immobilized onto a microtiter plate. GST-PcrV was immobilized onto a microtiter plate overnight at 4° C. The plate was washed and all unadsorbed sites blocked with the addition of block/diluent buffer for at least 60 minutes. After washing the plate, analytes were dispensed onto the pre-coated microtiter plate and incubated for at least 60 minutes. The plate was washed and a solution containing a biotinylated antibody specific to the humaneered Fab was added for 45 minutes. The plate was washed and a HRP— conjugate solution added for 30 minutes. After the final wash step, a tetramethylbenzidine (TMB) peroxidase substrate solution was added and incubated for approximately 6 minutes. The reaction was stopped with a phosphoric acid solution. Color develops in proportion to the amount of pegylated Fab present. Plates were read on a plate reader using two filters (450 nm for detection and 620 nm for background). Concentrations were determined on a standard curve obtained by plotting optical density (OD) versus concentration. The calibration curve was generated using a four-parameter logistic fit. The range for this method in human serum is from 0.200 to 12.8 ng/mL in 1% serum (20.0 ng/mL to 1280 ng/mL in 100% serum).

| Pharmacokinetic Profile of Humaneered Antibody in Human Subjects | | | | | |
|---|---|---|---|---|---|
| PK Parameter | Units | n | 1.0 mg/kg Cohort 1 | 3.0 mg/kg Cohort 2 | 10.0 mg/kg Cohort 3 |
| AUC(0-t) | ng * hr/mL | 4 | 10440826 (1137824) | 33973664 (2930669) | 120424224 (17896301) |
| AUC(0-∞) | ng * hr/mL | 4 | 10737696 (1235316) | 34856666 (3216244) | 124429066 (19035293) |
| % Extrap | (%) | 4 | 2.72 (0.886) | 2.49 (0.935) | 3.17 (0.461) |
| Cmax | (ng/mL) | 4 | 29334 (2039) | 93533 (10738) | 347287 (64571) |
| T½ | (hr) | 4 | 341 (38.5) | 310 (37.9) | 338 (14.1) |
| CL | (L/hr) | 4 | 0.00693 (0.000823) | 0.00556 (0.000573) | 0.00473 (0.00112) |
| Vz | (L) | 4 | 3.44 (0.730) | 2.50 (0.504) | 2.31 (0.588) |

The humaneered antibody had a terminal plasma half-life of approximately 14 days.

The presence of anti-drug antibodies, i.e., antibodies generated to the humaneered antibody, was tested at: pre-infusion, day 8, day 15 day 29 and day 70 post infusion. Anti-drug antibodies were measured using an electrochemiluminescent assay (ECLA). Positive controls and negative control serum were diluted 1:25 with diluent buffer. The controls were further diluted 1:2 by the addition of an equal volume of 0.8% acetic acid (resulting in 2× solutions) and then incubated at ambient temperature for approximately 15 minutes. Samples were then diluted an additional 1:2 with Label Master Mix (Antibody-Biotin and Antibody-SulfoTag at 0.5 μg/mL final working concentrations) resulting in a final 1:100 dilution. All controls were then incubated for one hour at room temperature with gentle shaking. The Streptavidin-coated standard MA2400 96-well microtiter plate was blocked by adding diluent buffer for 60 minutes. Diluent buffer was removed from plate wells by aspiration and controls were added to the plate and incubated for 60 minutes. The plate was aspirated and washed, and 1X MesoScaleDiscovery® (MSD) Read Buffer T with surfactant was added. The plates were read on an MSD electrochemiluminescence detector within 1 minute. Intensity of relative light units (RLU) produced are in proportion to the amount of anti-drug antibody present No anti-drug antibodies were detected at any time point. This example thus demonstrates that there was no detectable immunogenicity of the humaneered antibody in humans.

The following provides an exemplary listing of anti-PcrV antibody V-regions of the invention:

```
Exemplary Anti-PcrV V-regions
Vh (VH1)                                     SEQ ID NO: 1
EIQLVQSGAEVKKPGASVKVSCKASGYTFTDHAISWVRQAPGQGLEWMGW

ISPYSGNPNYAQSLQGRVSLTTDRSTRTAYMELRSLKSDDTAVYYCARNR

GDIYYDFTYAFDIWGQGTMVTVSS

VkI                                          SEQ ID NO: 2
DIQMTQSPSSVSASVGDRVTITCRASQGISSWLAWYQQKPGRAPKLLIYA

ASSLQSGVPSRFSGSGSGTGFTLTISSLQPEDVATYYCQQFWSTPYTFGQ

GTKLEIK
```

-continued

```
Vh                                           SEQ ID NO: 3
QVQLVESGGGVVQPGGSLRLSCAASGFTFSTAGMHWVRQAPGKGLEWVAV

IWYNGKEISYADSVKGRFTVSRDNPKNTLYLQMSSLRTEDTAVYYCARNR

GDIYYDFTYAMDIWGQGTMVTVSS

VkI                                          SEQ ID NO: 4
DIQMTQSPSSLSASVGDRVTITCRASQSISRWVAWYQQRPGKAPNLLIYD

ASSLKSGVPSRFSGSGSGTEFTLTISSLQPEDIATYYCQQFWSTPYTFGQ

GTKLEIK

Vh                                           SEQ ID NO: 5
QVQLVESGGGVVQPGRSLRLSCTASGFSFSSYGMHWVRQAPGKGLEWVAV

IWYNGKEISYADSVKGRFTVSRDNPKNTLYLQMSSLRTEDTAVYYCARNR

GDIYYDFTYAMDIWGQGTMVTVSS

VkI                                          SEQ ID NO: 6
AIQLTQSPSFLSASVGDRVTITCRASQGISTYLAWYQQKPGKPKLLIYAA

SSLQSGVPSRFSGSGSGTDFTLTISSLQPEDVATYYCQQFWSTPYTFGQG

TKLEIK

Vh                                           SEQ ID NO: 7
QVQLVESGGGLVQPGRSLRLSCVGSGFTFSSYGIHWVRQAPGKGLEWVAV

IWYNGKEISYADSVKGRFTVSRDNLKNTLYLQMSSLRTEDTAVYYCARNR

GDIYYDFTYAMDIWGQGTMVTVSS

VkI                                          SEQ ID NO: 8
DIQMTQSPSFLSASVGDRVTITCRASQGISTYLAWYQQKRGKAPKLLISA

ASSLQSGVPSRFSGSVSGTDFTLTISSLQSEDFAVYYCQQFWSTPYTFGQ

GTKLEIK

Vh                                           SEQ ID NO: 9
QVQLVESGGGLVQPGRSLRLSCVGSGFTFSSYGIHWVRQAPGKGLEWVAV

IWYNGKEISYADSVKGRFTVSRDNPKNTLYLQMSSLRTEDTAVYYCARNR

GDIYYDFTYAMDIWGQGTMVTVSS

VkI                                          SEQ ID NO: 10
DIQLTQSPSFLSASVGDRVTITCRASQGISTYLAWYQQKPGKAPKLLIYD

ASALQSGVPSRFSGSGSGTEFTLTISSLQPEDVATYYCQQFWSTPYTFGQ

GTKLEIK

Vh
EVQLVESGGGVVQPGGSLRLSCAASGFTFSTAGMHWVRQAPGKGLEWVAV

IWYNGKEISYADSVKGRFTVFRDNPKNTLYLQMSSLRTEDTAVYYCARNR

GDIYYDFTYAMDIWGQGTMVTVSS

VkI                                          SEQ ID NO: 12
DIQMTQSPSSLSASVGDRVTITCRASQSISRWVAWYQQRPGKAPNLLIYD

ASSLKSGVPSRFSGSGSGTEFTLTISSLQPEDIATYYCQQFWSTPYTFGQ

GTKLEIK

Vh                                           SEQ ID NO: 13
QVQLVESGGGVVQPGRSLRLSCAASGFTFSSYPLHWVRQAPGKGLEWVSF

ISYDGSEKYYASSVKGRFTISRDNSENTLYLQMNSLRPEDTAVYYCAPNR

GDIYYDFTYAMDIWGQGTMVTVSS
```

-continued

Vk SEQ ID NO: 14
DIQLTQSPSFLSASVGDRVTITCRASQGISTYLAWYQQKPGKAPKLLIYD

ASALQSGVPSRFSGSGSGTEFTLTISSLQPEDVATYYCQQFWSTPYTFGQ

GTKLEIK

Vh SEQ ID NO: 15
EVQLVESGGGVVQPGRSLRLSCTASGFSFSSYGMHWVRQAPGKGLEWVAV

IWYDGRNKYYADSVKGRFTISRDNSKNTLYLQMNSLPAEDTAVYYCARNR

GDIYYDFTYANDIWGQGTMVTVSS

VkIII SEQ ID NO: 16
EIVLTQFPGTLSLSPGERATLSCRASQNVGSAYLAWYQQKPGQAPRLLIY

GASRRAPGIPDRFSGSGSGTDFTLTINRLEPEDFAVYYCQQFWSTPYTFG

QGTKLEIK

Vh SEQ ID NO: 17
EVQLVESGGGVVQPGRSLRLSCAASGFTFSSYGMHWVRQAPGKGLEWVAV

IWYDGYNKDYADSVKGRFTISRDNSKRTLYLQINSLRAEDTAVYYCARNR

GDIYYDFTYAMDIWGQGTMVTVSS

VkIII SEQ ID NO: 18
EIVMTQSPATLSVSPGERATLSCRASQSVSSNLAWYQQKPGQAPRLLIYG

ASTRATGIPARFSGSGSGTEFTLTISSLQSEDFAVYYCQQFWSTPYTFGQ

GTKLEIK

Vh SEQ ID NO: 19
EVQLVESGGGVVQPGRSLRLSCAASGFTFSSYPLHWVRQAPGKGLEWVSF

ISYDGSEKYYASSVKGRFTISRDNSENTLYLQMNSLRPEDTAVYYCARNR

GDIYYDFTYAMDIWGQGTMVTVSS

VkIII SEQ ID NO: 20
EIVMTQSPATLSVSPGERATLSCRASQSVSSNLAWYQQKPGQAPRLLFYA

ASTRATGIPARFSGSGSGTEFTLTISSLQSEDFAVYYCQQFWSTPYTFGQ

GTKLEIK

Vh SEQ ID NO: 21
EVQLVESGGGLVQPGRSLRLSCVGSGFTFSSYGIHWVRQAPGKGLEWVAN

IWYDGSSESYIDSVKGRFTVSRDDSRNTVYLQMNSLRPEDTAVYYCARNR

GDIYYDFTYAMDIWGQGTMVTVSS

VkIII SEQ ID NO: 22
EIVMTQSPATLSVSPGERATLSCRASQSVSSNLAWYQQKPGQAPRLLIYG

ASTRATGIPARFSGSGSGTEFTLTISSLQSEDFAVYYCQQFWSTPYTFGQ

GTKLEIK

VH SEQ ID NO: 23
EVQLVESGGGVVQPGRSLRLSCAASGFTFSNYPMHWVRQAPGKGLEWVAV

ISYDGSEKWYADSVKGRFTISRDNSKNTLYLEMNSLRPEDTAVYYCARNR

GDIYYDFTYAMDQWGQGTTVTVSS

Vk SEQ ID NO: 24
DIQLTQSPSTLSASVGDSVTITCRASEGVDRWLAWYQQKPGRAPKLLIYD

ASTLQSGVPSRFSGSGSGTEFSLTISSLQPDDVATYYCQHFWGTPYTFGQ

GTKLEIK

-continued

VH SEQ ID NO: 25
EVQLVESGGGVVQPGRSLRLSCAASGFTFSNYPMHWVRQAPGKGLEWVAV

ISYDGSEKWYADSVKGRFTISRDNSKNTLYLEMNSLRPEDTAVYYCARNR

GDIYYDFTYAMDSWGQGTTVTVSS

VH SEQ ID NO: 26
EVQLVESGGGVVQPGRSLRLSCAASGFTFSNYPMHWVRQAPGKGLEWVAV

ISYDGSEKWYADSVKGRFTISRDNSKNTLYLEMNSLRPEDTAVYYCARNR

GDIYYDFTYAMDIWGQGTTVTVSS

VH SEQ ID NO: 35
EVQLVESGGGVVQPGRSLRLSCAASGFTFSNYPMHWVRQAPGKGLEWVAV

ISYDGSEKWYADSVKGRFTISRDNSKNTLYLEMNSLRPEDTAVYYCAPNR

GDIYYDFTYAMDYWGQGTTVTVSS

Vk SEQ ID NO: 36
DIQLTQSPSTLSASVGDSVTITCRASEGVDRWLAWYQQKPGRAPKLLIYD

ASTLQSGVPSRFSGSGSGTEFSLTISSLQPDDVATYYCQHFWSTPYTFGQ

GTKLEIK

V-regions of Exemplary Antibodies with Lambda light chain

Vh SEQ ID NO: 27
EVQLVESGGGVVQPGRSLRLSCAASGFTFSSYPLHWVRQAPGKGLEWVSF

ISYDGSEKYYASSVKGRFTISRDNSENTLYLQMNSLRPEDTAVYYCARNR

GDIYYDFTYAMDIWGQGTMVTVSS

Vl SEQ ID NO: 28
QSALTQPASVSGSPGQSITISCTGTSSDYVSWYQQHPGKAPKLIIYDVTN

RPSGVPDRFSGSKSGNTASLTISGLQAEDEADYYCQHFWSTPYTFGGGTK

Vh SEQ ID NO: 29
EVQLVESGGGVVQPGRSLRLSCAASGFTFSSYPLHWVRQAPGKGLEWVSF

ISYDGSEKYYASSVKGRFTISRDNSENTLYLQMNSLRPEDTAVYYCARNR

GDIYYDFTYAIVIDIWGQGTMVTVSS

Vl SEQ ID NO: 30
SSELTQDPAVSVALGQTVRITCQGDSLRSYYASWYQQKPGQAPVLVIYGK

NNRPSGIPDRFSGSSSGNTASLTITGAQAEDEADYYCQHFWSTPYTFGGG

TKLTVL

Additional $V_L$ regions:

Vl SEQ ID NO: 32
SSELTQDPAVSVALGQTVTITCQGDSLRSLYASWYQQKPGQAPVLVLYSK

NSRPSGIPDRFSGSSSGNTASLTITGARAEDEADYYCQHFWSTPYTFGGG

TKLTVL

Vl SEQ ID NO: 34
QSVLTQPPSASGSPGQSVTISCTGTSSDVGAYNYVSWYQQYPGKVPKLII

YEVTKRPSGVPDRFSGSKSGNTASLTVSGLRAEDEADYYCQHFWSTPYTF

GGGTKLTVL

VkI SEQ ID NO: 37
DIQMTQSPSSLSASVGDRVTITCRASQSISRWVAWYQQRPGKAPNLLIYD

ASSLKSGVPSRFSGSGSGTEFTLTISSLQPEDIATYYCQQFWGTPYTFGQ

GTKLEIK

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, accession numbers, patents, and patent applications cited in this specification are herein incorporated by reference as if each was specifically and individually indicated to be incorporated by reference.

What is claimed is:

1. An isolated anti-PcrV antibody that binds to PcrV, comprising:

a $V_H$ region that comprises a CDR3 having a sequence NRGDIYYDFTYAMDI (SEQ ID NO:99), a CDR2 sequence VISYDGSEKWYADSVKG (SEQ ID NO:57), and a CDR1 sequence NYPMH (SEQ ID NO:54); and a $V_L$ region that comprises a CDR3 having a sequence QHFWGTPYT (SEQ ID NO:110), a CDR2 sequence DASTLQS (SEQ ID NO:73) and a CDR1 sequence RASEGVDRWLA (SEQ ID NO:69).

2. The antibody of claim 1, wherein the $V_H$ region comprises the amino acid sequence of the V-segment region of SEQ ID NO:26.

3. The antibody of claim 2, wherein the $V_H$ region comprises the amino acid sequence set forth in SEQ ID NO:26.

4. The antibody of claim 1, wherein the $V_L$ region comprises the amino acid sequence of the V-segment of SEQ ID NO:24.

5. The antibody of claim 4, wherein the $V_L$ region comprises the amino acid sequence set forth in SEQ ID NO:24.

6. The antibody of claim 1, wherein the antibody is a Fab' fragment.

7. The antibody of claim 1, wherein the antibody is an IgG.

8. The antibody of claim 1, wherein the antibody is PEGylated.

9. The antibody of claim 8, wherein the antibody is di-PEGylated.

10. The antibody of claim 1, wherein the $V_H$ region or the $V_L$ region, or both the $V_H$ and $V_L$ region amino acid sequences comprise a methionine at the N-terminus.

11. An isolated anti-PcrV antibody that is an antagonist of the Type III secretion system, comprising: a $V_H$ region having the amino acid sequence set forth in SEQ ID NO:26 and a $V_L$ region having the amino acid sequence set forth in SEQ ID NO:24.

12. The antibody of claim 11, wherein the $V_H$ region or the $V_L$ region, or both the $V_H$ and $V_L$ regions have a methionine present at the N-terminus.

13. The antibody of claim 11, wherein the antibody is a di-PEGylated Fab'.

14. A composition comprising the isolated antibody of claim 11 and a pharmaceutically acceptable carrier.

15. A composition comprising the isolated antibody of claim 1 and a pharmaceutically acceptable carrier.

* * * * *

SEQUENCE LISTING

```
<160> NUMBER OF SEQ ID NOS: 119

<210> SEQ ID NO 1
<211> LENGTH: 124
<212> TYPE: PRT
<213> ORGANISM: Artificial Sequence
<220> FEATURE:
<223> OTHER INFORMATION: synthetic anti-PcrV antibody Vh (VH1) V-region

<400> SEQUENCE: 1

Glu Ile Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp His
            20                  25                  30

Ala Ile Ser Trp Val Arg Gln Ala Pro Gly Gln Gly Leu Glu Trp Met
        35                  40                  45

Gly Trp Ile Ser Pro Tyr Ser Gly Asn Pro Asn Tyr Ala Gln Ser Leu
    50                  55                  60

Gln Gly Arg Val Ser Leu Thr Thr Asp Arg Ser Thr Arg Thr Ala Tyr
65                  70                  75                  80

Met Glu Leu Arg Ser Leu Lys Ser Asp Asp Thr Ala Val Tyr Tyr Cys
                85                  90                  95

Ala Arg Asn Arg Gly Asp Ile Tyr Tyr Asp Phe Thr Tyr Ala Phe Asp
            100                 105                 110

Ile Trp Gly Gln Gly Thr Met Val Thr Val Ser Ser
        115                 120


<210> SEQ ID NO 2
<211> LENGTH: 107
<212> TYPE: PRT
<213> ORGANISM: Artificial Sequence
<220> FEATURE:
<223> OTHER INFORMATION: synthetic anti-PcrV antibody VkappaI V-region

<400> SEQUENCE: 2

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Val Ala Thr Tyr Tyr Cys Gln Gln Phe Trp Ser Thr Pro Tyr
                85                  90                  95

Thr Phe Gly Gln Gly Thr Lys Leu Glu Ile Lys
            100                 105


<210> SEQ ID NO 3
<211> LENGTH: 124
<212> TYPE: PRT
<213> ORGANISM: Artificial Sequence
```

<220> FEATURE:
<223> OTHER INFORMATION: synthetic anti-PcrV antibody Vh V-region

<400> SEQUENCE: 3

```
Gln Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Ser Thr Ala
            20                  25                  30

Gly Met His Trp Val Arg Gln Ala Pro Gly Lys Gly Leu Glu Trp Val
        35                  40                  45

Ala Val Ile Trp Tyr Asn Gly Lys Glu Ile Ser Tyr Ala Asp Ser Val
    50                  55                  60

Lys Gly Arg Phe Thr Val Ser Arg Asp Asn Pro Lys Asn Thr Leu Tyr
65                  70                  75                  80

Leu Gln Met Ser Ser Leu Arg Thr Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120
```

<210> SEQ ID NO 4
<211> LENGTH: 107
<212> TYPE: PRT
<213> ORGANISM: Artificial Sequence
<220> FEATURE:
<223> OTHER INFORMATION: synthetic anti-PcrV antibody VkappaI V-region

<400> SEQUENCE: 4

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Arg Trp
            20                  25                  30

Val Ala Trp Tyr Gln Gln Arg Pro Gly Lys Ala Pro Asn Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Ile Ala Thr Tyr Tyr Cys Gln Gln Phe Trp Ser Thr Pro Tyr
                85                  90                  95

Thr Phe Gly Gln Gly Thr Lys Leu Glu Ile Lys
            100                 105
```

<210> SEQ ID NO 5
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 5

```
Gln Val Gln Leu Val Glu Ser Gly Gly Gly Val Val Gln Pro Gly Arg
 1               5                  10                  15

Ser Leu Arg Leu Ser Cys Thr Ala Ser Gly Phe Ser Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asn Gly Lys Glu Ile Ser Tyr Ala Asp Ser Val
```

-continued

```
    50                  55                  60

Lys Gly Arg Phe Thr Val Ser Arg Asp Asn Pro Lys Asn Thr Leu Tyr
65                  70                  75                  80

Leu Gln Met Ser Ser Leu Arg Thr Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120


<210> SEQ ID NO 6
<211> LENGTH: 107
<212> TYPE: PRT
<213> ORGANISM: Artificial Sequence
<220> FEATURE:
<223> OTHER INFORMATION: synthetic anti-PcrV antibody VkappaI V-region

<400> SEQUENCE: 6

Ala Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Phe Trp Ser Thr Pro Tyr
                85                  90                  95

Thr Phe Gly Gln Gly Thr Lys Leu Glu Ile Lys
            100                 105


<210> SEQ ID NO 7
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 7

Gln Val Gln Leu Val Glu Ser Gly Gly Gly Leu Val Gln Pro Gly Arg
 1               5                  10                  15

Ser Leu Arg Leu Ser Cys Val Gly Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Trp Tyr Asn Gly Lys Glu Ile Ser Tyr Ala Asp Ser Val
    50                  55                  60

Lys Gly Arg Phe Thr Val Ser Arg Asp Asn Leu Lys Asn Thr Leu Tyr
65                  70                  75                  80

Leu Gln Met Ser Ser Leu Arg Thr Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120
```

-continued

<210> SEQ ID NO 8
<211> LENGTH: 107
<212> TYPE: PRT
<213> ORGANISM: Artificial Sequence
<220> FEATURE:
<223> OTHER INFORMATION: synthetic anti-PcrV antibody VkappaI V-region

<400> SEQUENCE: 8

```
Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ser Thr Tyr
            20                  25                  30

Leu Ala Trp Tyr Gln Gln Lys Arg Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Val Ser Gly Thr Asp Phe Thr Leu Thr Ile Ser Ser Leu Gln Ser
65                  70                  75                  80

Glu Asp Phe Ala Val Tyr Tyr Cys Gln Gln Phe Trp Ser Thr Pro Tyr
                85                  90                  95

Thr Phe Gly Gln Gly Thr Lys Leu Glu Ile Lys
            100                 105
```

<210> SEQ ID NO 9
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 9

```
Gln Val Gln Leu Val Glu Ser Gly Gly Gly Leu Val Gln Pro Gly Arg
 1               5                  10                  15

Ser Leu Arg Leu Ser Cys Val Gly Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Trp Tyr Asn Gly Lys Glu Ile Ser Tyr Ala Asp Ser Val
    50                  55                  60

Lys Gly Arg Phe Thr Val Ser Arg Asp Asn Pro Lys Asn Thr Leu Tyr
65                  70                  75                  80

Leu Gln Met Ser Ser Leu Arg Thr Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120
```

<210> SEQ ID NO 10
<211> LENGTH: 107
<212> TYPE: PRT
<213> ORGANISM: Artificial Sequence
<220> FEATURE:
<223> OTHER INFORMATION: synthetic anti-PcrV antibody VkappaI V-region

<400> SEQUENCE: 10

```
Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ser Thr Tyr
            20                  25                  30
```

```
Leu Ala Trp Tyr Gln Gln Lys Pro Gly Lys Ala Pro Lys Leu Leu Ile
        35                  40                  45

Tyr Asp Ala Ser Ala Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Val Ala Thr Tyr Tyr Cys Gln Gln Phe Trp Ser Thr Pro Tyr
                85                  90                  95

Thr Phe Gly Gln Gly Thr Lys Leu Glu Ile Lys
            100                 105


<210> SEQ ID NO 11
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 11

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Ser Thr Ala
            20                  25                  30

Gly Met His Trp Val Arg Gln Ala Pro Gly Lys Gly Leu Glu Trp Val
        35                  40                  45

Ala Val Ile Trp Tyr Asn Gly Lys Glu Ile Ser Tyr Ala Asp Ser Val
    50                  55                  60

Lys Gly Arg Phe Thr Val Phe Arg Asp Asn Pro Lys Asn Thr Leu Tyr
65                  70                  75                  80

Leu Gln Met Ser Ser Leu Arg Thr Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120


<210> SEQ ID NO 12
<211> LENGTH: 107
<212> TYPE: PRT
<213> ORGANISM: Artificial Sequence
<220> FEATURE:
<223> OTHER INFORMATION: synthetic anti-PcrV antibody VkappaI V-region

<400> SEQUENCE: 12

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Arg Trp
            20                  25                  30

Val Ala Trp Tyr Gln Gln Arg Pro Gly Lys Ala Pro Asn Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Ile Ala Thr Tyr Tyr Cys Gln Gln Phe Trp Ser Thr Pro Tyr
                85                  90                  95

Thr Phe Gly Gln Gly Thr Lys Leu Glu Ile Lys
            100                 105
```

-continued

<210> SEQ ID NO 13
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 13

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Pro Leu His Trp Val Arg Gln Ala Pro Gly Lys Gly Leu Glu Trp Val
        35                  40                  45

Ser Phe Ile Ser Tyr Asp Gly Ser Glu Lys Tyr Tyr Ala Ser Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120
```

<210> SEQ ID NO 14
<211> LENGTH: 107
<212> TYPE: PRT
<213> ORGANISM: Artificial Sequence
<220> FEATURE:
<223> OTHER INFORMATION: synthetic anti-PcrV antibody Vkappa V-region

<400> SEQUENCE: 14

```
Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Lys Ala Pro Lys Leu Leu Ile
        35                  40                  45

Tyr Asp Ala Ser Ala Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Val Ala Thr Tyr Tyr Cys Gln Gln Phe Trp Ser Thr Pro Tyr
                85                  90                  95

Thr Phe Gly Gln Gly Thr Lys Leu Glu Ile Lys
            100                 105
```

<210> SEQ ID NO 15
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 15

```
Glu Val Gln Leu Val Glu Ser Gly Gly Gly Val Val Gln Pro Gly Arg
 1               5                  10                  15

Ser Leu Arg Leu Ser Cys Thr Ala Ser Gly Phe Ser Phe Ser Ser Tyr
            20                  25                  30
```

```
Gly Met His Trp Val Arg Gln Ala Pro Gly Lys Gly Leu Glu Trp Val
        35                  40                  45

Ala Val Ile Trp Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120


<210> SEQ ID NO 16
<211> LENGTH: 108
<212> TYPE: PRT
<213> ORGANISM: Artificial Sequence
<220> FEATURE:
<223> OTHER INFORMATION: synthetic anti-PcrV antibody VkappaIII V-region

<400> SEQUENCE: 16

Glu Ile Val Leu Thr Gln Phe Pro Gly Thr Leu Ser Leu Ser Pro Gly
 1               5                  10                  15

Glu Arg Ala Thr Leu Ser Cys Arg Ala Ser Gln Asn Val Gly Ser Ala
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Pro Gly Ile Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln Gln Phe Trp Ser Thr Pro
                85                  90                  95

Tyr Thr Phe Gly Gln Gly Thr Lys Leu Glu Ile Lys
            100                 105


<210> SEQ ID NO 17
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 17

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Tyr Asn Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110
```

```
Ile Trp Gly Gln Gly Thr Met Val Thr Val Ser Ser
        115                 120


<210> SEQ ID NO 18
<211> LENGTH: 107
<212> TYPE: PRT
<213> ORGANISM: Artificial Sequence
<220> FEATURE:
<223> OTHER INFORMATION: synthetic anti-PcrV antibody VkappaIII V-region

<400> SEQUENCE: 18

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Phe Trp Ser Thr Pro Tyr
                85                  90                  95

Thr Phe Gly Gln Gly Thr Lys Leu Glu Ile Lys
            100                 105


<210> SEQ ID NO 19
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 19

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Pro Leu His Trp Val Arg Gln Ala Pro Gly Lys Gly Leu Glu Trp Val
        35                  40                  45

Ser Phe Ile Ser Tyr Asp Gly Ser Glu Lys Tyr Tyr Ala Ser Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120


<210> SEQ ID NO 20
<211> LENGTH: 107
<212> TYPE: PRT
<213> ORGANISM: Artificial Sequence
<220> FEATURE:
<223> OTHER INFORMATION: synthetic anti-PcrV antibody VkappaIII V-region

<400> SEQUENCE: 20

Glu Ile Val Met Thr Gln Ser Pro Ala Thr Leu Ser Val Ser Pro Gly
```

-continued

```
 1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Phe
        35                  40                  45

Tyr Ala Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Phe Trp Ser Thr Pro Tyr
                85                  90                  95

Thr Phe Gly Gln Gly Thr Lys Leu Glu Ile Lys
            100                 105


<210> SEQ ID NO 21
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 21

Glu Val Gln Leu Val Glu Ser Gly Gly Gly Leu Val Gln Pro Gly Arg
 1               5                   10                  15

Ser Leu Arg Leu Ser Cys Val Gly Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Asn Ile Trp Tyr Asp Gly Ser Ser Glu Ser Tyr Ile Asp Ser Val
    50                  55                  60

Lys Gly Arg Phe Thr Val Ser Arg Asp Asp Ser Arg Asn Thr Val Tyr
65                  70                  75                  80

Leu Gln Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120


<210> SEQ ID NO 22
<211> LENGTH: 107
<212> TYPE: PRT
<213> ORGANISM: Artificial Sequence
<220> FEATURE:
<223> OTHER INFORMATION: synthetic anti-PcrV antibody VkappaIII V-region

<400> SEQUENCE: 22

Glu Ile Val Met Thr Gln Ser Pro Ala Thr Leu Ser Val Ser Pro Gly
 1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Phe Trp Ser Thr Pro Tyr
```

-continued

```
                85                  90                  95

Thr Phe Gly Gln Gly Thr Lys Leu Glu Ile Lys
            100                 105


<210> SEQ ID NO 23
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 23

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
            20                  25                  30

Pro Met His Trp Val Arg Gln Ala Pro Gly Lys Gly Leu Glu Trp Val
        35                  40                  45

Ala Val Ile Ser Tyr Asp Gly Ser Glu Lys Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Gln Trp Gly Gln Gly Thr Thr Val Thr Val Ser Ser
        115                 120


<210> SEQ ID NO 24
<211> LENGTH: 107
<212> TYPE: PRT
<213> ORGANISM: Artificial Sequence
<220> FEATURE:
<223> OTHER INFORMATION: synthetic anti-PcrV antibody Vkappa V-region

<400> SEQUENCE: 24

Asp Ile Gln Leu Thr Gln Ser Pro Ser Thr Leu Ser Ala Ser Val Gly
 1               5                  10                  15

Asp Ser Val Thr Ile Thr Cys Arg Ala Ser Glu Gly Val Asp Arg Trp
            20                  25                  30

Leu Ala Trp Tyr Gln Gln Lys Pro Gly Arg Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Val Ala Thr Tyr Tyr Cys Gln His Phe Trp Gly Thr Pro Tyr
                85                  90                  95

Thr Phe Gly Gln Gly Thr Lys Leu Glu Ile Lys
            100                 105


<210> SEQ ID NO 25
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 25
```

```
Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
            20                  25                  30

Pro Met His Trp Val Arg Gln Ala Pro Gly Lys Gly Leu Glu Trp Val
        35                  40                  45

Ala Val Ile Ser Tyr Asp Gly Ser Glu Lys Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ser Trp Gly Gln Gly Thr Thr Val Thr Val Ser Ser
        115                 120
```

<210> SEQ ID NO 26
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 26

```
Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
            20                  25                  30

Pro Met His Trp Val Arg Gln Ala Pro Gly Lys Gly Leu Glu Trp Val
        35                  40                  45

Ala Val Ile Ser Tyr Asp Gly Ser Glu Lys Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Thr Val Thr Val Ser Ser
        115                 120
```

<210> SEQ ID NO 27
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 27

```
Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Pro Leu His Trp Val Arg Gln Ala Pro Gly Lys Gly Leu Glu Trp Val
        35                  40                  45

Ser Phe Ile Ser Tyr Asp Gly Ser Glu Lys Tyr Tyr Ala Ser Ser Val
    50                  55                  60
```

```
Lys Gly Arg Phe Thr Ile Ser Arg Asp Asn Ser Glu Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120


<210> SEQ ID NO 28
<211> LENGTH: 104
<212> TYPE: PRT
<213> ORGANISM: Artificial Sequence
<220> FEATURE:
<223> OTHER INFORMATION: synthetic anti-PcrV antibody Vlambda V-region

<400> SEQUENCE: 28

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Tyr Val Ser Trp
            20                  25                  30

Tyr Gln Gln His Pro Gly Lys Ala Pro Lys Leu Ile Ile Tyr Asp Val
        35                  40                  45

Thr Asn Arg Pro Ser Gly Val Pro Asp Arg Phe Ser Gly Ser Lys Ser
    50                  55                  60

Gly Asn Thr Ala Ser Leu Thr Ile Ser Gly Leu Gln Ala Glu Asp Glu
65                  70                  75                  80

Ala Asp Tyr Tyr Cys Gln His Phe Trp Ser Thr Pro Tyr Thr Phe Gly
                85                  90                  95

Gly Gly Thr Lys Leu Thr Val Leu
            100


<210> SEQ ID NO 29
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 29

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Pro Leu His Trp Val Arg Gln Ala Pro Gly Lys Gly Leu Glu Trp Val
        35                  40                  45

Ser Phe Ile Ser Tyr Asp Gly Ser Glu Lys Tyr Tyr Ala Ser Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120


<210> SEQ ID NO 30
<211> LENGTH: 106
```

<212> TYPE: PRT
<213> ORGANISM: Artificial Sequence
<220> FEATURE:
<223> OTHER INFORMATION: synthetic anti-PcrV antibody Vlambda V-region

<400> SEQUENCE: 30

```
Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Gln His Phe Trp Ser Thr Pro Tyr Thr
                85                  90                  95

Phe Gly Gly Gly Thr Lys Leu Thr Val Leu
            100                 105
```

<210> SEQ ID NO 31

<400> SEQUENCE: 31

000

<210> SEQ ID NO 32
<211> LENGTH: 106
<212> TYPE: PRT
<213> ORGANISM: Artificial Sequence
<220> FEATURE:
<223> OTHER INFORMATION: synthetic anti-PcrV antibody Vlambda V-region

<400> SEQUENCE: 32

```
Ser Ser Glu Leu Thr Gln Asp Pro Ala Val Ser Val Ala Leu Gly Gln
 1               5                  10                  15

Thr Val Thr Ile Thr Cys Gln Gly Asp Ser Leu Arg Ser Leu Tyr Ala
            20                  25                  30

Ser Trp Tyr Gln Gln Lys Pro Gly Gln Ala Pro Val Leu Val Leu Tyr
        35                  40                  45

Ser Lys Asn Ser Arg Pro Ser Gly Ile Pro Asp Arg Phe Ser Gly Ser
    50                  55                  60

Ser Ser Gly Asn Thr Ala Ser Leu Thr Ile Thr Gly Ala Arg Ala Glu
65                  70                  75                  80

Asp Glu Ala Asp Tyr Tyr Cys Gln His Phe Trp Ser Thr Pro Tyr Thr
                85                  90                  95

Phe Gly Gly Gly Thr Lys Leu Thr Val Leu
            100                 105
```

<210> SEQ ID NO 33

<400> SEQUENCE: 33

000

<210> SEQ ID NO 34
<211> LENGTH: 109
<212> TYPE: PRT
<213> ORGANISM: Artificial Sequence
<220> FEATURE:
<223> OTHER INFORMATION: synthetic anti-PcrV antibody Vlambda V-region

<400> SEQUENCE: 34

Gln Ser Val Leu Thr Gln Pro Pro Ser Ala Ser Gly Ser Pro Gly Gln
1 5 10 15

Ser Val Thr Ile Ser Cys Thr Gly Thr Ser Ser Asp Val Gly Ala Tyr
20 25 30

Asn Tyr Val Ser Trp Tyr Gln Gln Tyr Pro Gly Lys Val Pro Lys Leu
35 40 45

Ile Ile Tyr Glu Val Thr Lys Arg Pro Ser Gly Val Pro Asp Arg Phe
50 55 60

Ser Gly Ser Lys Ser Gly Asn Thr Ala Ser Leu Thr Val Ser Gly Leu
65 70 75 80

Arg Ala Glu Asp Glu Ala Asp Tyr Tyr Cys Gln His Phe Trp Ser Thr
85 90 95

Pro Tyr Thr Phe Gly Gly Gly Thr Lys Leu Thr Val Leu
100 105

<210> SEQ ID NO 35
<211> LENGTH: 124
<212> TYPE: PRT
<213> ORGANISM: Artificial Sequence
<220> FEATURE:
<223> OTHER INFORMATION: synthetic anti-PcrV antibody Vh V-region

<400> SEQUENCE: 35

Glu Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Asn Tyr
20 25 30

Pro Met His Trp Val Arg Gln Ala Pro Gly Lys Gly Leu Glu Trp Val
35 40 45

Ala Val Ile Ser Tyr Asp Gly Ser Glu Lys Trp Tyr Ala Asp Ser Val
50 55 60

Lys Gly Arg Phe Thr Ile Ser Arg Asp Asn Ser Lys Asn Thr Leu Tyr
65 70 75 80

Leu Glu Met Asn Ser Leu Arg Pro Glu Asp Thr Ala Val Tyr Tyr Cys
85 90 95

Ala Arg Asn Arg Gly Asp Ile Tyr Tyr Asp Phe Thr Tyr Ala Met Asp
100 105 110

Tyr Trp Gly Gln Gly Thr Thr Val Thr Val Ser Ser
115 120

<210> SEQ ID NO 36
<211> LENGTH: 107
<212> TYPE: PRT
<213> ORGANISM: Artificial Sequence
<220> FEATURE:
<223> OTHER INFORMATION: synthetic anti-PcrV antibody Vkappa V-region

<400> SEQUENCE: 36

Asp Ile Gln Leu Thr Gln Ser Pro Ser Thr Leu Ser Ala Ser Val Gly
1 5 10 15

Asp Ser Val Thr Ile Thr Cys Arg Ala Ser Glu Gly Val Asp Arg Trp
20 25 30

Leu Ala Trp Tyr Gln Gln Lys Pro Gly Arg Ala Pro Lys Leu Leu Ile
35 40 45

Tyr Asp Ala Ser Thr Leu Gln Ser Gly Val Pro Ser Arg Phe Ser Gly
50 55 60

Ser Gly Ser Gly Thr Glu Phe Ser Leu Thr Ile Ser Ser Leu Gln Pro
65 70 75 80

Asp Asp Val Ala Thr Tyr Tyr Cys Gln His Phe Trp Ser Thr Pro Tyr
85 90 95

Thr Phe Gly Gln Gly Thr Lys Leu Glu Ile Lys
100 105

<210> SEQ ID NO 37
<211> LENGTH: 107
<212> TYPE: PRT
<213> ORGANISM: Artificial Sequence
<220> FEATURE:
<223> OTHER INFORMATION: synthetic anti-PcrV antibody VkappaI V-region

<400> SEQUENCE: 37

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Arg Trp
20 25 30

Val Ala Trp Tyr Gln Gln Arg Pro Gly Lys Ala Pro Asn Leu Leu Ile
35 40 45

Tyr Asp Ala Ser Ser Leu Lys Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Ile Ala Thr Tyr Tyr Cys Gln Gln Phe Trp Gly Thr Pro Tyr
85 90 95

Thr Phe Gly Gln Gly Thr Lys Leu Glu Ile Lys
100 105

<210> SEQ ID NO 38
<211> LENGTH: 11
<212> TYPE: PRT
<213> ORGANISM: Artificial Sequence
<220> FEATURE:
<223> OTHER INFORMATION: synthetic anti-PcrV antibody binding specificity determinant (BSD) in CDRH3

<400> SEQUENCE: 38

Asn Arg Gly Asp Ile Tyr Tyr Asp Phe Thr Tyr
1 5 10

<210> SEQ ID NO 39
<211> LENGTH: 5
<212> TYPE: PRT
<213> ORGANISM: Artificial Sequence
<220> FEATURE:
<223> OTHER INFORMATION: synthetic anti-PcrV antibody binding specificity determinant (BSD) in CDRL3
<220> FEATURE:
<221> NAME/KEY: VARIANT
<222> LOCATION: (3)...(3)
<223> OTHER INFORMATION: Xaa = Ser or Gly

<400> SEQUENCE: 39

Phe Trp Xaa Thr Pro
1 5

<210> SEQ ID NO 40
<211> LENGTH: 5
<212> TYPE: PRT
<213> ORGANISM: Artificial Sequence
<220> FEATURE:
<223> OTHER INFORMATION: synthetic anti-PcrV antibody CDR3

<400> SEQUENCE: 40

Phe Trp Gly Thr Pro
 1               5

<210> SEQ ID NO 41
<211> LENGTH: 9
<212> TYPE: PRT
<213> ORGANISM: Artificial Sequence
<220> FEATURE:
<223> OTHER INFORMATION: synthetic anti-PcrV antibody V-L region CDR3
<220> FEATURE:
<221> NAME/KEY: VARIANT
<222> LOCATION: (2)...(2)
<223> OTHER INFORMATION: Xaa = Gln or His

<400> SEQUENCE: 41

Gln Xaa Phe Trp Gly Thr Pro Tyr Thr
 1               5

<210> SEQ ID NO 42
<211> LENGTH: 15
<212> TYPE: PRT
<213> ORGANISM: Artificial Sequence
<220> FEATURE:
<223> OTHER INFORMATION: synthetic anti-PcrV antibody V-H region CDR3
<220> FEATURE:
<221> NAME/KEY: VARIANT
<222> LOCATION: (13)...(13)
<223> OTHER INFORMATION: Xaa = Met or Phe
<220> FEATURE:
<221> NAME/KEY: VARIANT
<222> LOCATION: (15)...(15)
<223> OTHER INFORMATION: Xaa = Ile, Gln, Tyr or Ser

<400> SEQUENCE: 42

Asn Arg Gly Asp Ile Tyr Tyr Asp Phe Thr Tyr Ala Xaa Asp Xaa
 1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: synthetic anti-PcrV antibody V-H region CDR3
<220> FEATURE:
<221> NAME/KEY: VARIANT
<222> LOCATION: (15)...(15)
<223> OTHER INFORMATION: Xaa = Ile, Gln, Tyr or Ser

<400> SEQUENCE: 43

Asn Arg Gly Asp Ile Tyr Tyr Asp Phe Thr Tyr Ala Met Asp Xaa
 1               5                   10                  15

<210> SEQ ID NO 44
<211> LENGTH: 11
<212> TYPE: PRT
<213> ORGANISM: Artificial Sequence
<220> FEATURE:
<223> OTHER INFORMATION: synthetic anti-PcrV antibody FR4 region

<400> SEQUENCE: 44

Trp Gly Gln Gly Thr Ser Val Thr Val Ser Ser
 1               5                   10

<210> SEQ ID NO 45
<211> LENGTH: 11
<212> TYPE: PRT
<213> ORGANISM: Artificial Sequence
<220> FEATURE:
<223> OTHER INFORMATION: synthetic anti-PcrV antibody V-H region FR4

<220> FEATURE:
<221> NAME/KEY: VARIANT
<222> LOCATION: (6)...(6)
<223> OTHER INFORMATION: Xaa = Thr or Met

<400> SEQUENCE: 45

Trp Gly Gln Gly Thr Xaa Val Thr Val Ser Ser
1 5 10

<210> SEQ ID NO 46
<211> LENGTH: 9
<212> TYPE: PRT
<213> ORGANISM: Artificial Sequence
<220> FEATURE:
<223> OTHER INFORMATION: synthetic anti-PcrV antibody light chain CDR3
<220> FEATURE:
<221> NAME/KEY: VARIANT
<222> LOCATION: (2)...(2)
<223> OTHER INFORMATION: Xaa = His or Gln
<220> FEATURE:
<221> NAME/KEY: VARIANT
<222> LOCATION: (5)...(5)
<223> OTHER INFORMATION: Xaa = Gly or Ser

<400> SEQUENCE: 46

Gln Xaa Phe Trp Xaa Thr Pro Tyr Thr
1 5

<210> SEQ ID NO 47
<211> LENGTH: 10
<212> TYPE: PRT
<213> ORGANISM: Artificial Sequence
<220> FEATURE:
<223> OTHER INFORMATION: synthetic anti-PcrV antibody V-L region FR4

<400> SEQUENCE: 47

Phe Gly Gln Gly Thr Lys Leu Glu Ile Lys
1 5 10

<210> SEQ ID NO 48
<211> LENGTH: 10
<212> TYPE: PRT
<213> ORGANISM: Artificial Sequence
<220> FEATURE:
<223> OTHER INFORMATION: synthetic anti-PcrV antibody V-L region FR4

<400> SEQUENCE: 48

Phe Gly Gly Gly Thr Lys Leu Thr Val Leu
1 5 10

<210> SEQ ID NO 49
<211> LENGTH: 17
<212> TYPE: PRT
<213> ORGANISM: Artificial Sequence
<220> FEATURE:
<223> OTHER INFORMATION: synthetic anti-PcrV antibody heavy chain region CDR2
<220> FEATURE:
<221> NAME/KEY: VARIANT
<222> LOCATION: (1)...(1)
<223> OTHER INFORMATION: Xaa = Val, Phe or Asn
<220> FEATURE:
<221> NAME/KEY: VARIANT
<222> LOCATION: (3)...(3)
<223> OTHER INFORMATION: Xaa = Ser or Trp
<220> FEATURE:
<221> NAME/KEY: VARIANT
<222> LOCATION: (7)...(7)
<223> OTHER INFORMATION: Xaa = Ser, Lys, Arg or Tyr
<220> FEATURE:
<221> NAME/KEY: VARIANT
<222> LOCATION: (8)...(8)

<223> OTHER INFORMATION: Xaa = Asn, Ser, Asp or Glu
<220> FEATURE:
<221> NAME/KEY: VARIANT
<222> LOCATION: (9)...(9)
<223> OTHER INFORMATION: Xaa = Lys, Ile or Glu
<220> FEATURE:
<221> NAME/KEY: VARIANT
<222> LOCATION: (10)...(10)
<223> OTHER INFORMATION: Xaa = Tyr, Ser, Asp or Trp
<220> FEATURE:
<221> NAME/KEY: VARIANT
<222> LOCATION: (12)...(12)
<223> OTHER INFORMATION: Xaa = Ala or Ile
<220> FEATURE:
<221> NAME/KEY: VARIANT
<222> LOCATION: (13)...(13)
<223> OTHER INFORMATION: Xaa = Asp or Ser

<400> SEQUENCE: 49

Xaa Ile Xaa Tyr Asx Gly Xaa Xaa Xaa Xaa Tyr Xaa Xaa Ser Val Lys
1 5 10 15

Gly

<210> SEQ ID NO 50
<211> LENGTH: 5
<212> TYPE: PRT
<213> ORGANISM: Artificial Sequence
<220> FEATURE:
<223> OTHER INFORMATION: synthetic anti-PcrV antibody CDR1

<400> SEQUENCE: 50

Thr Ala Gly Met His
1 5

<210> SEQ ID NO 51
<211> LENGTH: 5
<212> TYPE: PRT
<213> ORGANISM: Artificial Sequence
<220> FEATURE:
<223> OTHER INFORMATION: synthetic anti-PcrV antibody CDR1

<400> SEQUENCE: 51

Ser Tyr Gly Ile His
1 5

<210> SEQ ID NO 52
<211> LENGTH: 5
<212> TYPE: PRT
<213> ORGANISM: Artificial Sequence
<220> FEATURE:
<223> OTHER INFORMATION: synthetic anti-PcrV antibody CDR1

<400> SEQUENCE: 52

Ser Tyr Gly Met His
1 5

<210> SEQ ID NO 53
<211> LENGTH: 5
<212> TYPE: PRT
<213> ORGANISM: Artificial Sequence
<220> FEATURE:
<223> OTHER INFORMATION: synthetic anti-PcrV antibody CDR1

<400> SEQUENCE: 53

Ser Tyr Pro Leu His
1 5

<210> SEQ ID NO 54
<211> LENGTH: 5

<212> TYPE: PRT
<213> ORGANISM: Artificial Sequence
<220> FEATURE:
<223> OTHER INFORMATION: synthetic anti-PcrV antibody CDR1

<400> SEQUENCE: 54

Asn Tyr Pro Met His
1 5

<210> SEQ ID NO 55
<211> LENGTH: 17
<212> TYPE: PRT
<213> ORGANISM: Artificial Sequence
<220> FEATURE:
<223> OTHER INFORMATION: synthetic anti-PcrV antibody CDR2

<400> SEQUENCE: 55

Val Ile Trp Tyr Asn Gly Lys Glu Ile Ser Tyr Ala Asp Ser Val Lys
1 5 10 15

Gly

<210> SEQ ID NO 56
<211> LENGTH: 17
<212> TYPE: PRT
<213> ORGANISM: Artificial Sequence
<220> FEATURE:
<223> OTHER INFORMATION: synthetic anti-PcrV antibody CDR2

<400> SEQUENCE: 56

Phe Ile Ser Tyr Asp Gly Ser Glu Lys Tyr Tyr Ala Ser Ser Val Lys
1 5 10 15

Gly

<210> SEQ ID NO 57
<211> LENGTH: 17
<212> TYPE: PRT
<213> ORGANISM: Artificial Sequence
<220> FEATURE:
<223> OTHER INFORMATION: synthetic anti-PcrV antibody CDR2

<400> SEQUENCE: 57

Val Ile Ser Tyr Asp Gly Ser Glu Lys Trp Tyr Ala Asp Ser Val Lys
1 5 10 15

Gly

<210> SEQ ID NO 58
<211> LENGTH: 17
<212> TYPE: PRT
<213> ORGANISM: Artificial Sequence
<220> FEATURE:
<223> OTHER INFORMATION: synthetic anti-PcrV antibody CDR2

<400> SEQUENCE: 58

Val Ile Trp Tyr Asp Gly Arg Asn Lys Tyr Tyr Ala Asp Ser Val Lys
1 5 10 15

Gly

<210> SEQ ID NO 59
<211> LENGTH: 17
<212> TYPE: PRT
<213> ORGANISM: Artificial Sequence
<220> FEATURE:
<223> OTHER INFORMATION: synthetic anti-PcrV antibody CDR2

<400> SEQUENCE: 59

Val Ile Trp Tyr Asp Gly Tyr Asn Lys Asp Tyr Ala Asp Ser Val Lys
1 5 10 15

Gly

<210> SEQ ID NO 60
<211> LENGTH: 17
<212> TYPE: PRT
<213> ORGANISM: Artificial Sequence
<220> FEATURE:
<223> OTHER INFORMATION: synthetic anti-PcrV antibody CDR2

<400> SEQUENCE: 60

Asn Ile Trp Tyr Asp Gly Ser Ser Glu Ser Tyr Ile Asp Ser Val Lys
1 5 10 15

Gly

<210> SEQ ID NO 61
<211> LENGTH: 5
<212> TYPE: PRT
<213> ORGANISM: Artificial Sequence
<220> FEATURE:
<223> OTHER INFORMATION: synthetic anti-PcrV antibody VH region CDR1

<400> SEQUENCE: 61

Asp His Ala Ile Ser
1 5

<210> SEQ ID NO 62
<211> LENGTH: 17
<212> TYPE: PRT
<213> ORGANISM: Artificial Sequence
<220> FEATURE:
<223> OTHER INFORMATION: synthetic anti-PcrV antibody VH region CDR2

<400> SEQUENCE: 62

Trp Ile Ser Pro Tyr Ser Gly Asn Pro Asn Tyr Ala Gln Ser Leu Gln
1 5 10 15

Gly

<210> SEQ ID NO 63
<211> LENGTH: 15
<212> TYPE: PRT
<213> ORGANISM: Artificial Sequence
<220> FEATURE:
<223> OTHER INFORMATION: synthetic anti-PcrV antibody VH region CDR3

<400> SEQUENCE: 63

Asn Arg Gly Asp Ile Tyr Tyr Asp Phe Thr Tyr Ala Phe Asp Ile
1 5 10 15

<210> SEQ ID NO 64
<211> LENGTH: 11
<212> TYPE: PRT
<213> ORGANISM: Artificial Sequence
<220> FEATURE:
<223> OTHER INFORMATION: synthetic anti-PcrV antibody CDR1
<220> FEATURE:
<221> NAME/KEY: VARIANT
<222> LOCATION: (5)...(5)
<223> OTHER INFORMATION: Xaa = Ser or Gly
<220> FEATURE:
<221> NAME/KEY: VARIANT
<222> LOCATION: (6)...(6)
<223> OTHER INFORMATION: Xaa = Ile or Val
<220> FEATURE:
<221> NAME/KEY: VARIANT
<222> LOCATION: (7)...(7)
<223> OTHER INFORMATION: Xaa = Ser or Asp
<220> FEATURE:
<221> NAME/KEY: VARIANT
<222> LOCATION: (8)...(8)
<223> OTHER INFORMATION: Xaa = Ser, Arg or Thr
<220> FEATURE:
<221> NAME/KEY: VARIANT
<222> LOCATION: (9)...(9)
<223> OTHER INFORMATION: Xaa = Trp or Tyr
<220> FEATURE:
<221> NAME/KEY: VARIANT
<222> LOCATION: (10)...(10)
<223> OTHER INFORMATION: Xaa = Leu or Val

<400> SEQUENCE: 64

Arg Ala Ser Glx Xaa Xaa Xaa Xaa Xaa Xaa Ala
1 5 10

<210> SEQ ID NO 65
<211> LENGTH: 7
<212> TYPE: PRT
<213> ORGANISM: Artificial Sequence
<220> FEATURE:
<223> OTHER INFORMATION: synthetic anti-PcrV antibody CDR2
<220> FEATURE:
<221> NAME/KEY: VARIANT
<222> LOCATION: (1)...(1)
<223> OTHER INFORMATION: Xaa = Asp or Ala
<220> FEATURE:
<221> NAME/KEY: VARIANT
<222> LOCATION: (4)...(4)
<223> OTHER INFORMATION: Xaa = Ser, Ala or Thr
<220> FEATURE:
<221> NAME/KEY: VARIANT
<222> LOCATION: (6)...(6)
<223> OTHER INFORMATION: Xaa = Glu, Gln or Lys

<400> SEQUENCE: 65

Xaa Ala Ser Xaa Leu Xaa Ser
1 5

<210> SEQ ID NO 66
<211> LENGTH: 11
<212> TYPE: PRT
<213> ORGANISM: Artificial Sequence
<220> FEATURE:
<223> OTHER INFORMATION: synthetic anti-PcrV antibody CDR1

<400> SEQUENCE: 66

Arg Ala Ser Gln Gly Ile Ser Thr Tyr Leu Ala
1 5 10

<210> SEQ ID NO 67
<211> LENGTH: 11
<212> TYPE: PRT
<213> ORGANISM: Artificial Sequence
<220> FEATURE:
<223> OTHER INFORMATION: synthetic anti-PcrV antibody CDR1

<400> SEQUENCE: 67

Arg Ala Ser Gln Gly Ile Ser Ser Trp Leu Ala
1 5 10

<210> SEQ ID NO 68
<211> LENGTH: 11
<212> TYPE: PRT
<213> ORGANISM: Artificial Sequence
<220> FEATURE:
<223> OTHER INFORMATION: synthetic anti-PcrV antibody CDR1

<400> SEQUENCE: 68

Arg Ala Ser Gln Ser Ile Ser Arg Trp Val Ala 1 5 10

<210> SEQ ID NO 69
<211> LENGTH: 11
<212> TYPE: PRT
<213> ORGANISM: Artificial Sequence
<220> FEATURE:
<223> OTHER INFORMATION: synthetic anti-PcrV antibody CDR1

<400> SEQUENCE: 69

Arg Ala Ser Glu Gly Val Asp Arg Trp Leu Ala
1 5 10

<210> SEQ ID NO 70
<211> LENGTH: 7
<212> TYPE: PRT
<213> ORGANISM: Artificial Sequence
<220> FEATURE:
<223> OTHER INFORMATION: synthetic anti-PcrV antibody CDR2

<400> SEQUENCE: 70

Ala Ala Ser Ser Leu Gln Ser
1 5

<210> SEQ ID NO 71
<211> LENGTH: 7
<212> TYPE: PRT
<213> ORGANISM: Artificial Sequence
<220> FEATURE:
<223> OTHER INFORMATION: synthetic anti-PcrV antibody CDR2

<400> SEQUENCE: 71

Asp Ala Ser Ser Leu Lys Ser
1 5

<210> SEQ ID NO 72
<211> LENGTH: 7
<212> TYPE: PRT
<213> ORGANISM: Artificial Sequence
<220> FEATURE:
<223> OTHER INFORMATION: synthetic anti-PcrV antibody CDR2

<400> SEQUENCE: 72

Asp Ala Ser Ala Leu Gln Ser
1 5

<210> SEQ ID NO 73
<211> LENGTH: 7
<212> TYPE: PRT
<213> ORGANISM: Artificial Sequence
<220> FEATURE:
<223> OTHER INFORMATION: synthetic anti-PcrV antibody CDR2

<400> SEQUENCE: 73

Asp Ala Ser Thr Leu Gln Ser
1 5

<210> SEQ ID NO 74
<211> LENGTH: 12
<212> TYPE: PRT
<213> ORGANISM: Artificial Sequence
<220> FEATURE:
<223> OTHER INFORMATION: synthetic anti-PcrV antibody CDR1

<400> SEQUENCE: 74

Arg Ala Ser Asn Ser Val Gly Ala Tyr Asn Leu Ala
1 5 10

<210> SEQ ID NO 75
<211> LENGTH: 11
<212> TYPE: PRT
<213> ORGANISM: Artificial Sequence
<220> FEATURE:
<223> OTHER INFORMATION: synthetic anti-PcrV antibody CDR1

<400> SEQUENCE: 75

Arg Ala Ser Gln Ser Val Ser Ser Asn Leu Ala
 1               5                  10

<210> SEQ ID NO 76
<211> LENGTH: 7
<212> TYPE: PRT
<213> ORGANISM: Artificial Sequence
<220> FEATURE:
<223> OTHER INFORMATION: synthetic anti-PcrV antibody CDR2
<220> FEATURE:
<221> NAME/KEY: VARIANT
<222> LOCATION: (1)...(1)
<223> OTHER INFORMATION: Xaa = Ala or Gly
<220> FEATURE:
<221> NAME/KEY: VARIANT
<222> LOCATION: (4)...(4)
<223> OTHER INFORMATION: Xaa = Thr or Arg
<220> FEATURE:
<221> NAME/KEY: VARIANT
<222> LOCATION: (7)...(7)
<223> OTHER INFORMATION: Xaa = Thr or Pro

<400> SEQUENCE: 76

Xaa Ala Ser Xaa Arg Ala Xaa
 1               5

<210> SEQ ID NO 77
<211> LENGTH: 11
<212> TYPE: PRT
<213> ORGANISM: Artificial Sequence
<220> FEATURE:
<223> OTHER INFORMATION: synthetic anti-PcrV antibody CDR1
<220> FEATURE:
<221> NAME/KEY: VARIANT
<222> LOCATION: (8)...(8)
<223> OTHER INFORMATION: Xaa = Tyr or Leu

<400> SEQUENCE: 77

Gln Gly Asp Ser Leu Arg Ser Xaa Tyr Ala Ser
 1               5                  10

<210> SEQ ID NO 78
<211> LENGTH: 7
<212> TYPE: PRT
<213> ORGANISM: Artificial Sequence
<220> FEATURE:
<223> OTHER INFORMATION: synthetic anti-PcrV antibody CDR2
<220> FEATURE:
<221> NAME/KEY: VARIANT
<222> LOCATION: (1)...(1)
<223> OTHER INFORMATION: Xaa = Gly or Ser
<220> FEATURE:
<221> NAME/KEY: VARIANT
<222> LOCATION: (4)...(4)
<223> OTHER INFORMATION: Xaa = Asn or Ser

<400> SEQUENCE: 78

Xaa Lys Asn Xaa Arg Pro Ser
 1               5

<210> SEQ ID NO 79
<211> LENGTH: 14
<212> TYPE: PRT

```
<213> ORGANISM: Artificial Sequence
<220> FEATURE:
<223> OTHER INFORMATION: synthetic anti-PcrV antibody CDR1

<400> SEQUENCE: 79

Thr Gly Thr Ser Ser Asp Val Gly Ala Tyr Asn Tyr Val Ser
 1              5                   10


<210> SEQ ID NO 80
<211> LENGTH: 9
<212> TYPE: PRT
<213> ORGANISM: Artificial Sequence
<220> FEATURE:
<223> OTHER INFORMATION: synthetic anti-PcrV antibody CDR1

<400> SEQUENCE: 80

Thr Gly Thr Ser Ser Asp Tyr Val Ser
 1              5


<210> SEQ ID NO 81
<211> LENGTH: 7
<212> TYPE: PRT
<213> ORGANISM: Artificial Sequence
<220> FEATURE:
<223> OTHER INFORMATION: synthetic anti-PcrV antibody CDR2
<220> FEATURE:
<221> NAME/KEY: VARIANT
<222> LOCATION: (1)...(1)
<223> OTHER INFORMATION: Xaa = Glu or Asp
<220> FEATURE:
<221> NAME/KEY: VARIANT
<222> LOCATION: (4)...(4)
<223> OTHER INFORMATION: Xaa = Lys or Asn

<400> SEQUENCE: 81

Xaa Val Thr Xaa Arg Pro Ser
 1              5


<210> SEQ ID NO 82
<211> LENGTH: 113
<212> TYPE: PRT
<213> ORGANISM: Artificial Sequence
<220> FEATURE:
<223> OTHER INFORMATION: synthetic anti-PcrV antibody germ-line sequence
      VH1-18

<400> SEQUENCE: 82

Gln Val Gln Leu Val Gln Ser Gly Ala Glu Val Lys Lys Pro Gly Ala
 1              5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Phe Asp Ile Trp Gly Gln Gly Thr Met Val Thr Val Ser
            100                 105                 110

Ser


<210> SEQ ID NO 83
<211> LENGTH: 113
```

<212> TYPE: PRT
<213> ORGANISM: Artificial Sequence
<220> FEATURE:
<223> OTHER INFORMATION: synthetic anti-PcrV antibody germ-line sequence VH3-30.3

<400> SEQUENCE: 83

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Phe Asp Ile Trp Gly Gln Gly Thr Met Val Thr Val Ser
            100                 105                 110

Ser
```

<210> SEQ ID NO 84
<211> LENGTH: 15
<212> TYPE: PRT
<213> ORGANISM: Artificial Sequence
<220> FEATURE:
<223> OTHER INFORMATION: synthetic anti-PcrV antibody germ-line JH6

<400> SEQUENCE: 84

```
Gly Met Asp Val Trp Gly Gln Gly Thr Thr Val Thr Val Ser Ser
 1               5                  10                  15
```

<210> SEQ ID NO 85
<211> LENGTH: 107
<212> TYPE: PRT
<213> ORGANISM: Artificial Sequence
<220> FEATURE:
<223> OTHER INFORMATION: synthetic anti-PcrV antibody germ-line sequence VkappaI L12

<400> SEQUENCE: 85

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys
            100                 105
```

<210> SEQ ID NO 86
<211> LENGTH: 107
<212> TYPE: PRT

-continued

<213> ORGANISM: Artificial Sequence
<220> FEATURE:
<223> OTHER INFORMATION: synthetic anti-PcrV antibody VkappaIII L2

<400> SEQUENCE: 86

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys
            100                 105
```

<210> SEQ ID NO 87
<211> LENGTH: 108
<212> TYPE: PRT
<213> ORGANISM: Artificial Sequence
<220> FEATURE:
<223> OTHER INFORMATION: synthetic anti-PcrV antibody VkappaIII V-region

<400> SEQUENCE: 87

```
Glu Ile Val Leu Thr Gln Phe Pro Gly Thr Leu Ser Leu Ser Pro Gly
 1               5                  10                  15

Glu Arg Ala Thr Leu Ser Cys Arg Ala Ser Asn Ser Val Gly Ala Tyr
            20                  25                  30

Asn Leu Ala Trp Tyr Gln Gln Lys Pro Gly Gln Ala Pro Arg Leu Leu
        35                  40                  45

Ile Tyr Gly Ala Ser Arg Arg Ala Pro Gly Ile Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln Gln Phe Trp Ser Thr Pro
                85                  90                  95

Tyr Thr Phe Gly Gln Gly Thr Lys Leu Glu Ile Lys
            100                 105
```

<210> SEQ ID NO 88
<211> LENGTH: 108
<212> TYPE: PRT
<213> ORGANISM: Artificial Sequence
<220> FEATURE:
<223> OTHER INFORMATION: synthetic anti-PcrV antibody germ-line sequence
VL3 31

<400> SEQUENCE: 88

```
Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60
```

```
Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105


<210> SEQ ID NO 89
<211> LENGTH: 111
<212> TYPE: PRT
<213> ORGANISM: Artificial Sequence
<220> FEATURE:
<223> OTHER INFORMATION: synthetic anti-PcrV antibody germ-line VL2 2c

<400> SEQUENCE: 89

Gln Ser Ala Leu Thr Gln Pro Pro Ser Ala Ser Gly Ser Pro Gly Gln
 1               5                  10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe Val Val Phe Gly Gly Gly Thr Lys Leu Thr Val Leu
            100                 105                 110


<210> SEQ ID NO 90
<211> LENGTH: 109
<212> TYPE: PRT
<213> ORGANISM: Artificial Sequence
<220> FEATURE:
<223> OTHER INFORMATION: synthetic anti-PcrV antibody Vlambda V-region

<400> SEQUENCE: 90

Gln Ser Val Leu Thr Gln Pro Pro Ser Ala Ser Gly Ser Pro Gly Gln
 1               5                  10                  15

Ser Val Thr Ile Ser Cys Thr Gly Thr Ser Ser Asp Val Gly Ala Tyr
            20                  25                  30

Asn Tyr Val Ser Trp Tyr Gln Gln Tyr Pro Gly Lys Val Pro Lys Leu
        35                  40                  45

Ile Ile Tyr Glu Val Thr Lys Arg Pro Ser Gly Val Pro Asp Arg Phe
    50                  55                  60

Ser Gly Ser Lys Ser Gly Asn Thr Ala Ser Leu Thr Val Ser Gly Arg
65                  70                  75                  80

Gln Ala Glu Asp Glu Ala Asp Tyr Tyr Cys Gln His Phe Trp Ser Thr
                85                  90                  95

Pro Tyr Thr Phe Gly Gly Gly Thr Lys Leu Thr Val Leu
            100                 105


<210> SEQ ID NO 91
<211> LENGTH: 114
<212> TYPE: PRT
<213> ORGANISM: Artificial Sequence
<220> FEATURE:
<223> OTHER INFORMATION: synthetic anti-PcrV antibody heavy chain
      constant region for Fd'
```

<400> SEQUENCE: 91

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala
```

<210> SEQ ID NO 92
<211> LENGTH: 107
<212> TYPE: PRT
<213> ORGANISM: Artificial Sequence
<220> FEATURE:
<223> OTHER INFORMATION: synthetic anti-PcrV antibody light chain (kappa) constant region

<400> SEQUENCE: 92

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 93
<211> LENGTH: 15
<212> TYPE: PRT
<213> ORGANISM: Artificial Sequence
<220> FEATURE:
<223> OTHER INFORMATION: synthetic anti-PcrV antibody heavy chain CDR3
<220> FEATURE:
<221> NAME/KEY: VARIANT
<222> LOCATION: (13)...(13)
<223> OTHER INFORMATION: Xaa = Met or Phe
<220> FEATURE:
<221> NAME/KEY: VARIANT
<222> LOCATION: (15)...(15)
<223> OTHER INFORMATION: Xaa = Ile, Ser or Gln

<400> SEQUENCE: 93

```
Asn Arg Gly Asp Ile Tyr Tyr Asp Phe Thr Tyr Ala Xaa Asp Xaa
 1               5                  10                  15
```

<210> SEQ ID NO 94
<211> LENGTH: 11
<212> TYPE: PRT
<213> ORGANISM: Artificial Sequence
<220> FEATURE:
<223> OTHER INFORMATION: synthetic anti-PcrV antibody FR4 sequence

<400> SEQUENCE: 94

```
Trp Gly Gln Gly Thr Met Val Thr Val Ser Ser
 1               5                  10
```

<210> SEQ ID NO 95
<211> LENGTH: 11
<212> TYPE: PRT
<213> ORGANISM: Artificial Sequence
<220> FEATURE:
<223> OTHER INFORMATION: synthetic anti-PcrV antibody FR4 sequence

<400> SEQUENCE: 95

```
Trp Gly Gln Gly Thr Thr Val Thr Val Ser Ser
 1               5                  10
```

<210> SEQ ID NO 96
<211> LENGTH: 26
<212> TYPE: PRT
<213> ORGANISM: Artificial Sequence
<220> FEATURE:
<223> OTHER INFORMATION: synthetic anti-PcrV antibody combination of
CDRH3 and FR4 sequences

<400> SEQUENCE: 96

```
Asn Arg Gly Asp Ile Tyr Tyr Asp Phe Thr Tyr Ala Phe Asp Ile Trp
 1               5                  10                  15

Gly Gln Gly Thr Met Val Thr Val Ser Ser
            20                  25
```

<210> SEQ ID NO 97
<211> LENGTH: 26
<212> TYPE: PRT
<213> ORGANISM: Artificial Sequence
<220> FEATURE:
<223> OTHER INFORMATION: synthetic anti-PcrV antibody combination of
CDRH3 and FR4 sequences

<400> SEQUENCE: 97

```
Asn Arg Gly Asp Ile Tyr Tyr Asp Phe Thr Tyr Ala Met Asp Ile Trp
 1               5                  10                  15

Gly Gln Gly Thr Met Val Thr Val Ser Ser
            20                  25
```

<210> SEQ ID NO 98
<211> LENGTH: 26
<212> TYPE: PRT
<213> ORGANISM: Artificial Sequence
<220> FEATURE:
<223> OTHER INFORMATION: synthetic anti-PcrV antibody combination of
CDRH3 and FR4 sequences

<400> SEQUENCE: 98

```
Asn Arg Gly Asp Ile Tyr Tyr Asp Phe Thr Tyr Ala Met Asp Ile Trp
 1               5                  10                  15

Gly Gln Gly Thr Thr Val Thr Val Ser Ser
            20                  25
```

<210> SEQ ID NO 99
<211> LENGTH: 15
<212> TYPE: PRT

<213> ORGANISM: Artificial Sequence
<220> FEATURE:
<223> OTHER INFORMATION: synthetic anti-PcrV antibody CDR3

<400> SEQUENCE: 99

Asn Arg Gly Asp Ile Tyr Tyr Asp Phe Thr Tyr Ala Met Asp Ile
1 5 10 15

<210> SEQ ID NO 100
<211> LENGTH: 15
<212> TYPE: PRT
<213> ORGANISM: Artificial Sequence
<220> FEATURE:
<223> OTHER INFORMATION: synthetic anti-PcrV antibody CDR3
<220> FEATURE:
<221> NAME/KEY: VARIANT
<222> LOCATION: (13)...(13)
<223> OTHER INFORMATION: Xaa = Met or Phe
<220> FEATURE:
<221> NAME/KEY: VARIANT
<222> LOCATION: (15)...(15)
<223> OTHER INFORMATION: Xaa = Gln or Ser

<400> SEQUENCE: 100

Asn Arg Gly Asp Ile Tyr Tyr Asp Phe Thr Tyr Ala Xaa Asp Xaa
1 5 10 15

<210> SEQ ID NO 101
<211> LENGTH: 19
<212> TYPE: PRT
<213> ORGANISM: Artificial Sequence
<220> FEATURE:
<223> OTHER INFORMATION: synthetic anti-PcrV antibody kappa chain
CDRL3-FR4 combination

<400> SEQUENCE: 101

Gln Gln Phe Trp Ser Thr Pro Tyr Thr Phe Gly Gln Gly Thr Lys Leu
1 5 10 15

Glu Ile Lys

<210> SEQ ID NO 102
<211> LENGTH: 19
<212> TYPE: PRT
<213> ORGANISM: Artificial Sequence
<220> FEATURE:
<223> OTHER INFORMATION: synthetic anti-PcrV antibody kappa chain
CDRL3-FR4 combination

<400> SEQUENCE: 102

Gln His Phe Trp Gly Thr Pro Tyr Thr Phe Gly Gln Gly Thr Lys Leu
1 5 10 15

Glu Ile Lys

<210> SEQ ID NO 103
<211> LENGTH: 19
<212> TYPE: PRT
<213> ORGANISM: Artificial Sequence
<220> FEATURE:
<223> OTHER INFORMATION: synthetic anti-PcrV antibody lambda chain
CDRL3-FR4 combination

<400> SEQUENCE: 103

Gln His Phe Trp Ser Thr Pro Tyr Thr Phe Gly Gly Gly Thr Lys Leu
1 5 10 15

Thr Val Leu

<210> SEQ ID NO 104

<211> LENGTH: 10
<212> TYPE: PRT
<213> ORGANISM: Artificial Sequence
<220> FEATURE:
<223> OTHER INFORMATION: synthetic anti-PcrV antibody CDR1

<400> SEQUENCE: 104

Gln Gly Asp Ser Leu Arg Ser Tyr Tyr Ala
1 5 10

<210> SEQ ID NO 105
<211> LENGTH: 8
<212> TYPE: PRT
<213> ORGANISM: Artificial Sequence
<220> FEATURE:
<223> OTHER INFORMATION: synthetic anti-PcrV antibody CDR1

<400> SEQUENCE: 105

Thr Gly Thr Ser Ser Asp Tyr Val
1 5

<210> SEQ ID NO 106
<211> LENGTH: 7
<212> TYPE: PRT
<213> ORGANISM: Artificial Sequence
<220> FEATURE:
<223> OTHER INFORMATION: synthetic anti-PcrV antibody CDR2

<400> SEQUENCE: 106

Gly Lys Asn Asn Arg Pro Ser
1 5

<210> SEQ ID NO 107
<211> LENGTH: 7
<212> TYPE: PRT
<213> ORGANISM: Artificial Sequence
<220> FEATURE:
<223> OTHER INFORMATION: synthetic anti-PcrV antibody CDR2

<400> SEQUENCE: 107

Glu Val Thr Lys Arg Pro Ser
1 5

<210> SEQ ID NO 108
<211> LENGTH: 7
<212> TYPE: PRT
<213> ORGANISM: Artificial Sequence
<220> FEATURE:
<223> OTHER INFORMATION: synthetic anti-PcrV antibody CDR2

<400> SEQUENCE: 108

Asp Val Thr Asn Arg Pro Ser
1 5

<210> SEQ ID NO 109
<211> LENGTH: 9
<212> TYPE: PRT
<213> ORGANISM: Artificial Sequence
<220> FEATURE:
<223> OTHER INFORMATION: synthetic anti-PcrV antibody CDR3

<400> SEQUENCE: 109

Gln Gln Phe Trp Ser Thr Pro Tyr Thr
1 5

<210> SEQ ID NO 110
<211> LENGTH: 9
<212> TYPE: PRT

-continued

<213> ORGANISM: Artificial Sequence
<220> FEATURE:
<223> OTHER INFORMATION: synthetic anti-PcrV antibody CDR3

<400> SEQUENCE: 110

Gln His Phe Trp Gly Thr Pro Tyr Thr
1 5

<210> SEQ ID NO 111
<211> LENGTH: 9
<212> TYPE: PRT
<213> ORGANISM: Artificial Sequence
<220> FEATURE:
<223> OTHER INFORMATION: synthetic anti-PcrV antibody CDR3

<400> SEQUENCE: 111

Gln His Phe Trp Ser Thr Pro Tyr Thr
1 5

<210> SEQ ID NO 112
<211> LENGTH: 9
<212> TYPE: PRT
<213> ORGANISM: Artificial Sequence
<220> FEATURE:
<223> OTHER INFORMATION: synthetic anti-PcrV antibody natural wild-type
human gamma-1 hinge for di-PEGylation

<400> SEQUENCE: 112

Thr His Thr Cys Pro Pro Cys Pro Ala
1 5

<210> SEQ ID NO 113
<211> LENGTH: 9
<212> TYPE: PRT
<213> ORGANISM: Artificial Sequence
<220> FEATURE:
<223> OTHER INFORMATION: synthetic anti-PcrV antibody Mutant Hinge-1 for
mono-PEGylation

<400> SEQUENCE: 113

Thr His Thr Ala Pro Pro Cys Pro Ala
1 5

<210> SEQ ID NO 114
<211> LENGTH: 9
<212> TYPE: PRT
<213> ORGANISM: Artificial Sequence
<220> FEATURE:
<223> OTHER INFORMATION: synthetic anti-PcrV antibody Mutant Hinge-2 for
mono-PEGylation

<400> SEQUENCE: 114

Thr His Thr Cys Pro Pro Ala Pro Ala
1 5

<210> SEQ ID NO 115
<211> LENGTH: 12
<212> TYPE: PRT
<213> ORGANISM: Artificial Sequence
<220> FEATURE:
<223> OTHER INFORMATION: synthetic anti-PcrV antibody Vkappa CDRL3 and
FR4

<400> SEQUENCE: 115

Tyr Thr Phe Gly Gln Gly Thr Lys Leu Glu Ile Lys
1 5 10

<210> SEQ ID NO 116

<211> LENGTH: 15
<212> TYPE: PRT
<213> ORGANISM: Artificial Sequence
<220> FEATURE:
<223> OTHER INFORMATION: synthetic anti-PcrV antibody V-H region CDR3
<220> FEATURE:
<221> NAME/KEY: VARIANT
<222> LOCATION: (13)...(13)
<223> OTHER INFORMATION: Xaa = Met or Phe

<400> SEQUENCE: 116

Asn Arg Gly Asp Ile Tyr Tyr Asp Phe Thr Tyr Ala Xaa Asp Ile
1 5 10 15

<210> SEQ ID NO 117
<211> LENGTH: 7
<212> TYPE: PRT
<213> ORGANISM: Artificial Sequence
<220> FEATURE:
<223> OTHER INFORMATION: synthetic anti-PcrV antibody V-L region CDR3
<220> FEATURE:
<221> NAME/KEY: VARIANT
<222> LOCATION: (3)...(3)
<223> OTHER INFORMATION: Xaa = Ser or Gly

<400> SEQUENCE: 117

Phe Trp Xaa Thr Pro Tyr Thr
1 5

<210> SEQ ID NO 118
<211> LENGTH: 14
<212> TYPE: PRT
<213> ORGANISM: Artificial Sequence
<220> FEATURE:
<223> OTHER INFORMATION: synthetic anti-PcrV antibody CDR1
<220> FEATURE:
<221> NAME/KEY: VARIANT
<222> LOCATION: (9)...(9)
<223> OTHER INFORMATION: Xaa = Gly or Ala

<400> SEQUENCE: 118

Thr Gly Thr Ser Ser Asp Val Gly Xaa Tyr Asn Tyr Val Ser
1 5 10

<210> SEQ ID NO 119
<211> LENGTH: 7
<212> TYPE: PRT
<213> ORGANISM: Artificial Sequence
<220> FEATURE:
<223> OTHER INFORMATION: synthetic anti-PcrV antibody CDR2
<220> FEATURE:
<221> NAME/KEY: VARIANT
<222> LOCATION: (1)...(1)
<223> OTHER INFORMATION: Xaa = Glu or Asp
<220> FEATURE:
<221> NAME/KEY: VARIANT
<222> LOCATION: (3)...(3)
<223> OTHER INFORMATION: Xaa = Ser or Thr
<220> FEATURE:
<221> NAME/KEY: VARIANT
<222> LOCATION: (4)...(4)
<223> OTHER INFORMATION: Xaa = Lys or Asn

<400> SEQUENCE: 119

Xaa Val Xaa Xaa Arg Pro Ser
1 5